US010849483B2

(12) United States Patent
Farr et al.

(10) Patent No.: US 10,849,483 B2
(45) Date of Patent: Dec. 1, 2020

(54) SINGLE-USE, PORT DEPLOYABLE ARTICULATING ENDOSCOPE

(71) Applicant: Vivid Medical, Inc., Palo Alto, CA (US)

(72) Inventors: Mina Farr, Palo Alto, CA (US); Shane James Kenney, Palo Alto, CA (US)

(73) Assignee: VIVID MEDICAL, INC., Palo Alto, CA (US)

( * ) Notice: Subject to any disclaimer, the term of this patent is extended or adjusted under 35 U.S.C. 154(b) by 371 days.

(21) Appl. No.: 14/853,242

(22) Filed: Sep. 14, 2015

(65) Prior Publication Data
US 2016/0073855 A1 Mar. 17, 2016

Related U.S. Application Data

(60) Provisional application No. 62/050,607, filed on Sep. 15, 2014.

(51) Int. Cl.
*A61B 1/00* (2006.01)
*A61B 1/06* (2006.01)
(Continued)

(52) U.S. Cl.
CPC ........ *A61B 1/00018* (2013.01); *A61B 1/0008* (2013.01); *A61B 1/0057* (2013.01);
(Continued)

(58) Field of Classification Search
CPC ... A61B 1/0051; A61B 1/0055; A61B 1/0057; A61B 1/008; A61B 1/05; A61B 1/051
See application file for complete search history.

(56) References Cited

U.S. PATENT DOCUMENTS 5,193,525 A * 3/1993 Silverstein ......... A61B 1/00096
600/123
5,415,158 A * 5/1995 Barthel .............. A61B 1/00165
600/149
(Continued)

FOREIGN PATENT DOCUMENTS

CN 103251434 A 8/2013
EP 2606812 A1 6/2013
(Continued)

OTHER PUBLICATIONS

International Search Report dated Jan. 21, 2016 as received in Application No. PCT/US 2015/050262.
(Continued)

*Primary Examiner* — Alexandra L Newton
(74) *Attorney, Agent, or Firm* — Maschoff Brennan

(57) ABSTRACT

The multi-section deployable and articulating endoscope is designed with tubing and flat cables that are small enough that the endoscope becomes a thin stick that is minimally invasive and usable with other devices in a common port. The endoscope includes very thin flat cables that are used for electrical connectivity and threaded above and below an articulation and deployment hinge for opening the endoscope passively using an adjustable tension spring, or by pulling on a first cable and closing the endoscope by pulling on a second cable, When in a tubular configuration the endoscope may be inserted into the port and an insufflation membrane inside the port forms an air seal with the endoscope, which aids in insufflation and desufflation. The endoscope includes one or more tubes for creating an air jet stream above the camera to act as a shield for keeping the camera clean.

20 Claims, 14 Drawing Sheets

(51) Int. Cl.
*A61B 1/005* (2006.01)
*A61B 1/05* (2006.01)
*A61B 1/313* (2006.01)
*A61M 13/00* (2006.01)

(52) U.S. Cl.
CPC ...... *A61B 1/00096* (2013.01); *A61B 1/00114* (2013.01); *A61B 1/00154* (2013.01); *A61B 1/00177* (2013.01); *A61B 1/05* (2013.01); *A61B 1/0615* (2013.01); *A61B 1/0676* (2013.01); *A61B 1/0684* (2013.01); *A61B 1/00029* (2013.01); *A61B 1/00045* (2013.01); *A61B 1/00091* (2013.01); *A61B 1/00103* (2013.01); *A61B 1/00124* (2013.01); *A61B 1/3132* (2013.01); *A61M 13/003* (2013.01)

(56) References Cited

U.S. PATENT DOCUMENTS

| | | | |
|---|---|---|---|
| 8,285,362 B2 | 10/2012 | Dietz et al. | |
| 8,517,927 B2 | 8/2013 | Asada et al. | |
| 8,562,516 B2 | 10/2013 | Saadat et al. | |
| 9,271,637 B2 | 3/2016 | Farr | |
| 9,339,264 B2 | 5/2016 | Piech et al. | |
| 2006/0074383 A1* | 4/2006 | Boulais | A61B 1/0052 604/95.04 |
| 2006/0193749 A1 | 8/2006 | Ghazarian et al. | |
| 2009/0318758 A1 | 12/2009 | Farr et al. | |
| 2010/0177193 A1 | 7/2010 | Flores | |
| 2011/0028790 A1 | 2/2011 | Farr et al. | |
| 2011/0288372 A1* | 11/2011 | Petersen | A61B 1/0008 600/109 |
| 2011/0301971 A1 | 12/2011 | Roesgh et al. | |
| 2011/0306831 A1* | 12/2011 | Kohnke | A61B 1/00071 600/109 |
| 2012/0143002 A1* | 6/2012 | Aranyi | A61B 1/00174 600/104 |
| 2012/0209070 A1* | 8/2012 | Piech | A61B 17/0293 600/110 |
| 2014/0135576 A1* | 5/2014 | Hebert | A61B 1/0057 600/109 |
| 2014/0213850 A1 | 7/2014 | Levy et al. | |
| 2017/0127915 A1* | 5/2017 | Viebach | A61B 1/00011 |

FOREIGN PATENT DOCUMENTS

| | | |
|---|---|---|
| IE | 20090923 A1 | 9/2010 |
| JP | 2002-119466 A | 4/2002 |
| JP | 2008-112248 A | 5/2008 |
| JP | 2008-514304 A | 5/2008 |
| JP | 2011-525842 A | 9/2011 |
| JP | 2013-180202 A | 9/2013 |
| WO | 2006/039511 A2 | 4/2006 |
| WO | 2009/144729 A1 | 12/2009 |
| WO | 2010/109696 A1 | 9/2010 |

OTHER PUBLICATIONS

Written Opinion of the International Searching Authority dated Jan. 21, 2016 as received in Application No. PCT/US2015/050262.
JP Office Action dated Apr. 24, 2018 as received in Application No. 2017-533743 [English Translation].
CN Office Action dated Mar. 5, 2018 as received in Application No. 201580057092 (English Translation).
Supplementary European Search Report dated Oct. 12, 2018 as received in Application No. 15 84 2859.
KR Office Action dated Oct. 18, 2018 as received in Application No. 10-2017-7010024 (Machine Translation).
AU Examination Report dated May 30, 2019 as received in Application No. 2015317883.
KR Notice of Allowance dated Feb. 25, 2019 as recived in Application No. 10-2017-7010024.
Indian Office Action issued in corresponding application No. 201717009641, dated Mar. 16, 2020.

\* cited by examiner

SINGLE-USE, PORT DEPLOYABLE ARTICULATING ENDOSCOPE

FIELD OF THE INVENTION

The specification relates generally to a disposable endoscope that can be used, for example, in minimally invasive surgical (MIS) procedures, general or diagnostic medical or industrial procedures. In some embodiments, the specification relates to a fully digital endoscope that is deployed after insertion through the endoscopic port which can also be articulated at various angles to provide, for example, zero degrees and up to 90 degrees or more angled scope functionality. The endoscope body, for example, may take up only a very small fraction of space inside the port once it is deployed, allowing other devices to be concurrently used inside the same port. Some embodiments of the invention may also include a deployable and/or articulating endoscope that may include a very small profile flexibly bent and extended to the side, at the proximal end of the port, and thus transparent to the user when other devices are inserted through the same port or other ports in the vicinity of the port. Some embodiments may also include a very small tube within the body of the articulating deployable endoscope for providing an air jet that creates a shield over a camera in the endoscope.

BACKGROUND

Endoscopy is used in both diagnostic and surgical procedures. Currently, MIS procedures, as opposed to open surgical procedures, are routinely done in almost all hospitals. MIS techniques minimize trauma to the patient by eliminating the need to make large incisions. This both reduces the risk of infection and reduces the patient's hospital stay. Endoscopic procedures in MIS use different types of endoscopes as imaging means, giving the surgeon an inside-the-body view of the surgical site. Specialized endoscopes are named depending on where they are intended to look. Examples include: cystoscope (bladder), nephroscope (kidney), bronchoscope (bronchi), laryngoscope (larynx+the voice box), otoscope (ear), arthroscope (joint), laparoscope (abdomen), gastrointestinal endoscopes, and specialized stereo endoscopes used as laparoscopes or for endoscopic cardiac surgery.

The endoscope may be inserted, for example, through a tiny surgical incision to view joints or organs in the chest or abdominal cavity. More often, the endoscope is inserted into a natural body orifice such as the nose, mouth, anus, bladder, or vagina. There are three basic types of endoscopes: rigid, semi-rigid, and flexible. The rigid endoscope comes in a variety of diameters, lengths, and various angles of view, such as zero, 30 or 70 deg. endoscopes and used depending on the requirements of the procedure. Typical endoscopic procedures require a large amount of equipment. The main equipment used in conjunction with the visual part of the endoscopic surgery are the endoscope body, fiber optics illumination bundles, illumination light source, light source controller, imaging camera, camera control module, and video display unit.

It can be advantageous to reduce the number of incisions as well as the size of the incision as much as possible in an endoscopic surgery. Normally a separate port is necessary to be used with a large diameter endoscope that takes the entire opening of the port, cannula or catheter once access to inside the body is obtained. Space is also very limited at the proximal end of the port and tools and endoscopes with proximal cameras are bulky and heavy, often propped up and locked in position with secondary mechanisms that often physically interfere with other devices used by the surgeon, especially if multiple ports are close to one another, or in Single-Port procedures.

During a surgical procedure, the scope may need to be exchanged with a different angle scope to look at an organ or surgical site from an angle, or to look behind an organ.

Another common problem that occurs with endoscopic procedures is that, because the endoscope is inserted into the body, the cavity being imaged by the endoscope is small and difficult to view. One way to obtain better images is to insufflate the cavity with gas to increase the volume of the area being imaged. Insufflation can be problematic because of inadequate seals between the port opening and the endoscopic device used. In addition, the smallness of the space may cause too much contact with the endoscope, which may result in the endoscope becoming smeared with blood and liquids that obscure the view for the camera on the endoscope to capture images of the cavity. In which case the procedure has to be stopped, the endoscope taken out, wiped clean and put back into the port to resume the procedure.

BRIEF SUMMARY

These and other limitations may be overcome by embodiments of the invention which relate to a disposable endoscope, or 2D or 3D endoscopic vision system that can be used in minimally invasive surgical procedures and/or diagnostic procedures. According to some embodiments, a multi jointed endoscope body may be reduced, for example, to a very small and flat, or a thin crescent shaped body at least in one section that is to be located inside a surgical port or cannula, and contains only very thin flat cables that are used as electrical connection means and/or as actuators for articulation and deployment. In some of the embodiments, the body of the endoscope, rather than the cylindrical body of a traditional endoscope, can be made rigid, may be malleable or flexible. In some embodiments, the endoscope body may be thin.

In some embodiments, the 2D or 3D endoscopic vision system at the distal section of the multi jointed endoscope body may be laid out such that illumination and vision modules may be facing the long side of the elongated distal section. This layout, may allow for more room, for multiple light sources (LEDs, Surface Emitting Vertical Cavity Lasers, or VCSELs of various colors), higher resolution single or multiple digital sensors, as well as larger higher Numerical Aperture, and FOV lens systems to fit in a smaller profile (cross section) of the endoscope. Thus, a much higher performance 2D-3D vision system can be inserted though a smaller diameter port. After deployment, for example, only minimal space inside the port is occupied by the endoscope with a secondary section of the endoscope remaining inside the port area.

In some embodiments, the body of the endoscope may also free up not only the space inside the port for insertion of other endoscopic devices and tools, but also is nearly transparent to the user at the proximal end, taking very little space with a flexible body that can be routed to the side of the port connecting to control electronics and displays through very flexible and thin cables. Multiple body endoscopes can also be inserted, for example, through the same port in various directions, where together they can provide a multi-axis and broadened view of the inside. In some embodiments, the images of the multiple endoscopes can be electronically stitched together to provide an extended FOV or individual endoscopes could be viewed separately by the same or various users.

In some embodiments, the endoscope may include one or more tubes for creating an air jet stream above the camera to act as a shield for keeping the camera clean. In some embodiments, an endoscope may include cables that are threaded above and below an articulation and deployment hinge for opening the endoscope by pulling on a first cable and closing the endoscope by pulling on a second cable. In some embodiments a single thin flat cable under spring tension can be routed to the distal articulating section and singularly used for deployment and articulation. In some embodiments, an endoscope may be designed with tubing and flat cables that are small enough such that the endoscope becomes a thin stick that is minimally invasive and usable with a secondary device inserted in the same port. In some embodiments the secondary section of the endoscope may be routed inside the wall of a port, or alternatively positioned inside grooves or slots on the wall of the port after insertion into the port. In some embodiments of the, the secondary section of the endoscope can be made malleable or flexible so it can be inserted through thin catheters with variable lengths. In some embodiments, the secondary section has a thin body.

In some embodiments, the endoscope may include a straight tubular configuration such that the endoscope may be inserted into the port, via a semi rigid or rigid insertion tube that opens and holds open the insufflation membrane within the port, acting as a guide for the endoscope. The port insufflation membrane, for example, may seal when the insertion tube is slid out of the port to the proximal end, exposing an airtight flexible tubular membrane on the scope body that is open in its distal end. The flexible tubular membrane opening towards the distal end, for example, may allow it to fill up with insufflation air from the inside of the body, thus expanding the membrane like a skirt inside the port, where the port insufflation membrane can form an air tight seal with the endoscope.

In some embodiments, a secondary device can be inserted into the same port, where the endoscope's small body and the air filled flexible tubular membrane can be pushed by the secondary endoscopic device to the side of the port, and where the endoscope and its air-filled membrane together with the secondary tool form an air tight seal with the insufflation membrane and mechanism of the port as well.

Once the endoscope is in position at the distal end of the port, in some embodiments, the endoscope can be deployed and articulated as needed by manipulating the flat cables. In some embodiments, the endoscope may act as a 0 deg. to 90 deg. endoscope. In some embodiments, if there is no other device inserted into the endoscope, the endoscope can be articulated further in the opposite direction (180 degrees from a 0 degrees endoscope) where the port can be made to look backwards toward the port itself or the anatomic wall at the incision site itself, or behind an organ with appropriate articulation.

In some embodiments, small flat cables may be made to work with a digital sensor with digital control electronics, with no interference with the video signal integrity where no special electrical shielding is used on the flat cables. Serial Mobile Industry Processor Interface (MIPI) output of the digital camera sensor may be used and the support electronics are split between the endoscope distal end electronics in close proximity of the digital sensor and on the same flex circuit, and the control electronics board at the proximal end of the endoscope flat cables.

In some embodiments, the same or similar flat cables can be used for deployment and articulation of the endoscope distal tip, where the actuation cables are routed inside the sliding tubes with low friction such as thin walled Polytetrafluoroethylene (PTFE) tube(s) that are housed within the body of the endoscope.

In some embodiments, the body of the endoscope can be made of a multi jointed very thin stainless sheet metal (acting as the skeleton of the multi jointed endoscope), where tiny stainless steel pins at various locations are welded to appropriate mating holes in the sheet metal. These pins, for example, can help hold the bent sheet metal skeleton of the endoscope together, and to flexibly hold its shape in the multiple endoscope sections. These pins can also act as functioning pivots and bending joints between various sheet metal sections of the endoscope, or additionally serve as guides for the electrical, deployment and articulation flat cables through the multi jointed endoscope body. At the distal section of the multi jointed endoscope, these pins, for example, can be used as a locking latch for the plastic body of the endoscope, or at the proximal section be used inside the proximal deployment and electrical housing, for positioning and locking of the electronics and deployment flat cables.

In some embodiments, a thin tubular flexible membrane that is open towards the distal end can be permanently mounted, with an air-tight seal, at the proximal end of the body section of the endoscope, which can be readily positioned within the port where the port insufflation membrane is positioned during use. The thin flexible membrane when inflated by the air from the insufflation, for example, can form an air-tight seal within the port insufflation membrane. The thin flexible membrane position, for example, can be chosen to accommodate various ports of different sizes, and can be long enough to accommodate ports with multiple insufflation membranes.

In some embodiments, the multi jointed endoscope can be equipped with a rigid or semi rigid insertion tube, that may be stored at the proximal section of the endoscope where it can, for example, be slid over the flexible tubular membrane from the proximal side (by unbending the proximal joint of the endoscope), to help open the port insufflation membrane and to protect the flexible tubular membrane during insertion into the port, as an insertion guide. Once the endoscope is in position inside the port, it is defined by the insertion tube plug at the proximal end of the rigid or semi-rigid tube, and as the port insufflation membrane is positioned safely over the flexible tubular membrane(s) of the port (still protected by the rigid insertion tube), the rigid insertion tube is then removed back over the endoscope body to its proximal resting position, while the port insufflation membrane is allowed to now press onto the flexible endoscope membrane, that is now inflated from its distal opening by the insufflation air from inside the body, to maintain an effective seal of the port.

In some embodiments, one or more multi jointed thin body endoscopes may be externally plugged into a control unit for display of endoscopic video (possibly through a USB hub), where the control unit provides power to the camera and light source(s) in the endoscope(s), and controls and displays the visual data, through universal serial bus (USB) cabling that can be disposed of along with the illumination and vision system and the endoscope. The control unit for the display of endoscopic data, could be an off-the-shelf computing unit, tablet, smart phone, or alike, where the control and display unit provides power to the endoscope and controls it as a USB device. The control and display unit with 3D viewing capability can be used, for example, with a single multi jointed body endoscope with dual cameras positioned and possibly separated by the illumination LEDs on the same distal section of the endoscope, where the stereo separation (3D inter-axial distance, mimicking the inter-ocular distance) of the stereo cameras can be adjusted to provide convenient stereoscopic viewing of the body based on the prevalent working distance of the endoscope.

In some embodiments, one or more of the deployment and articulation flat cables can be fixed in position at the distal tip, and can be under tension from the secured spring mechanism which is in turn under tension in the proximal section of the endoscope housing. The tension in the spring can be initially set, for example, while the distal portion of the endoscope is in the desired deployed position (maybe about 90 degrees from the endoscope body). The user can then straighten the distal section of the endoscope at the distal joint (where it is now along the rest of the endoscope body), and with the rigid guide tube over the flexible membrane, insert the endoscope through the insufflation membrane of the port, to access inside the body. This straightening of the distal section could apply further tension in the spring holding the deployment cable at the proximal end, thus when the hinged distal section reaches the distal end of the port and is free to bend back, it could passively spring back to its initial bend angle that is originally set by the spring tension, thereby releasing the extra tension applied by the user to straighten the distal section. Alternatively or in addition to the angular bend of the endoscope, the distal tip can be articulated or finely positioned with the simple manipulation of the spring mechanism at the proximal end, by further adjusting the tension (compressing or expanding the tension spring).

In some embodiments, the flat cables carrying the electrical signals and/or used as deployment and articulation cables, can be routed through a small thin-walled flexible tubular body in the secondary section of the endoscope, where the endoscope can be used as a flexible endoscope through a natural orifice or guided through a catheter. The flat cables can be routed straight through the flexible tubular body with flexibility in one direction, or spiraled around the wall of a flexible hollow tubular body to allow full flexibility of the endoscope body. In some embodiments, the secondary section of the endoscope can be thin.

In some embodiments, the deployable and articulating distal section, and/or the secondary section of the endoscope housing the flat cables can be made of multi jointed rigid sections, where each joint can take part in bending and articulation (together or separately) to allow for maximum flexibility and bend angle control of the endoscope.

In some embodiments multiple deployable and articulating endoscopes can be used in the same port in various directions that can be defined and maintained through structural mating features made in the port or access device, or by insertion of another device that guides and maintains the direction and relative positioning of multiple deployable and articulating endoscopes with one another.

This Summary is provided to introduce a selection of concepts in a simplified form that are further described below in the Detailed Description. The embodiments provided do not limit the disclosure but provide scenarios to aid understanding thereof. The Summary is not intended to identify key features or essential features of the claimed subject matter, nor is it intended to be used as an aid in determining the scope of the claimed subject matter.

BRIEF DESCRIPTION OF THE DRAWINGS

To further clarify the above and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 5 and 6. Illustrate the positioning of an insertion tube over a thin tubular insufflation membrane in preparation for insertion into a port;

FIG. 8 furthermore illustrates a rigid insertion tube now moved back to its proximal section resting location, allowing a thin tubular membrane of the endoscope to be inflated by the insufflation air, effectively plugging an insufflation membrane opening of a port;

FIG. 9 also illustrates an independent secondary tool inserted into a port, moving the endoscope midsection to the side of the port internal wall, and thereby sharing the same port space with the endoscope;

DETAILED DESCRIPTION

Example embodiments of the invention are directed to a deployable and/or articulating endoscope that includes a multi jointed housing, a camera, a light source at the distal section of the multi jointed endoscope, and very thin flat cables for electrical connections as well as deployment and articulation, which are routed through a secondary section of the endoscope, or incorporated within the outside body of another tool or surgical port.

Figure 1:
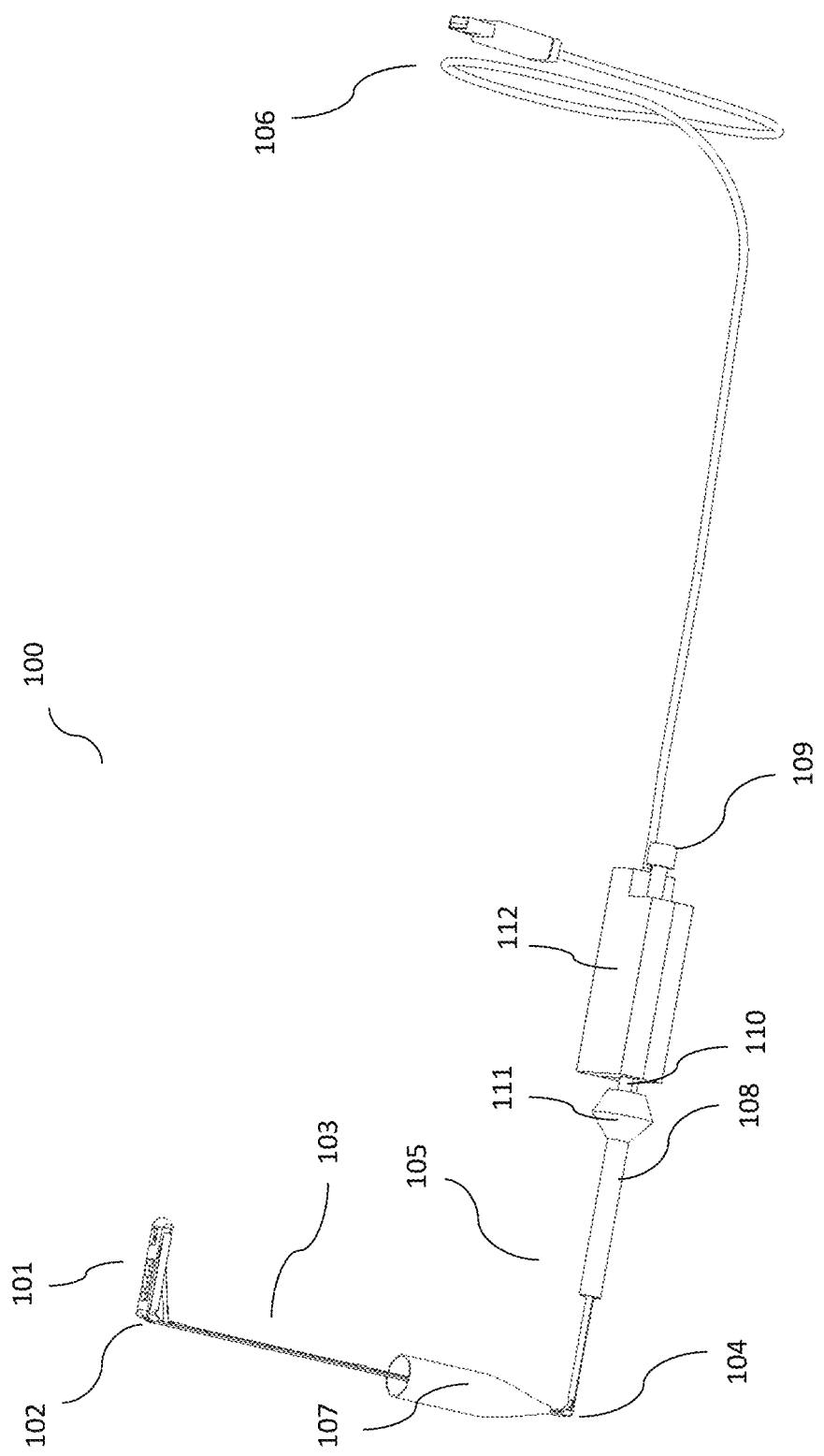
FIG. 1 illustrates a multi jointed single use port deployable articulating endoscope, with a distal section, a midsection that includes a thin tubular membrane as an insufflation air trap, a mechanical articulation control at a proximal section, and a USB interface for display and control.

FIG. 1 illustrates an example side view of a multi jointed endoscope 100, with a distal section 101, a secondary section which may include a midsection 103, and a proximal section 105. In some embodiments, the secondary section may be coupled with the distal section 101 via a distal joint (or joints) 102; and the midsection 103 and the proximal section 105 may be coupled together via a proximal joint 104. The distal section 101 of the endoscope 100, for example, may be bent at about a 90 degree angle at the distal joint 102, directing the endoscope illumination and camera modules, incorporated in the distal section 101, and thereby the vision system Field of View (FOV) directly in front of the midsection 103. In some embodiments, the midsection 103 can be a thin body that can be incorporated into other tubular surgical devices or ports. Distal joint 102 bending of the endoscope is set and controlled at the proximal section 105, using a tension spring mechanism incorporated inside a proximal housing 112. The passively bending, proximal joint 104, allows the proximal section 105 of the endoscope to be conveniently bent towards the side of the port when in use, and provide clearance around the port opening.

The endoscope 100 may include a multi jointed and formed thin sheet metal housing (or any other type of housing) at various sections of the endoscope 100 (distal section 101, midsection 103, and proximal section 105), coupled with passively bending, articulation and deployment hinges at the distal joint 102, and proximal joint 104, or any other section of the endoscope, that is coupled to a sheet metal body.

In some embodiments, the distal section 101 of the endoscope 100 can be 30-35 mm long. In other embodiments the distal section 101 can be 5-30 mm or 35-50 mm long. Additionally, the distal section 101 may have a diameter of 8-10 mm. Alternatively or additionally, the distal section 101 may have a diameter or 4-12 mm. In some embodiments the midsection 103 can be less than 1 mm in thickness, which may allow the endoscope 100 to be integrated or otherwise housed within the wall of a surgical port or flexible catheter. In other embodiments, the endoscope midsection 103 can be flexibly routed through a surgical body in a spiral fashion that has a diameter between 3-12 mm that is rigid, malleable, partially or fully flexible. In some embodiments, the midsection has a thin body.

Figure 2:
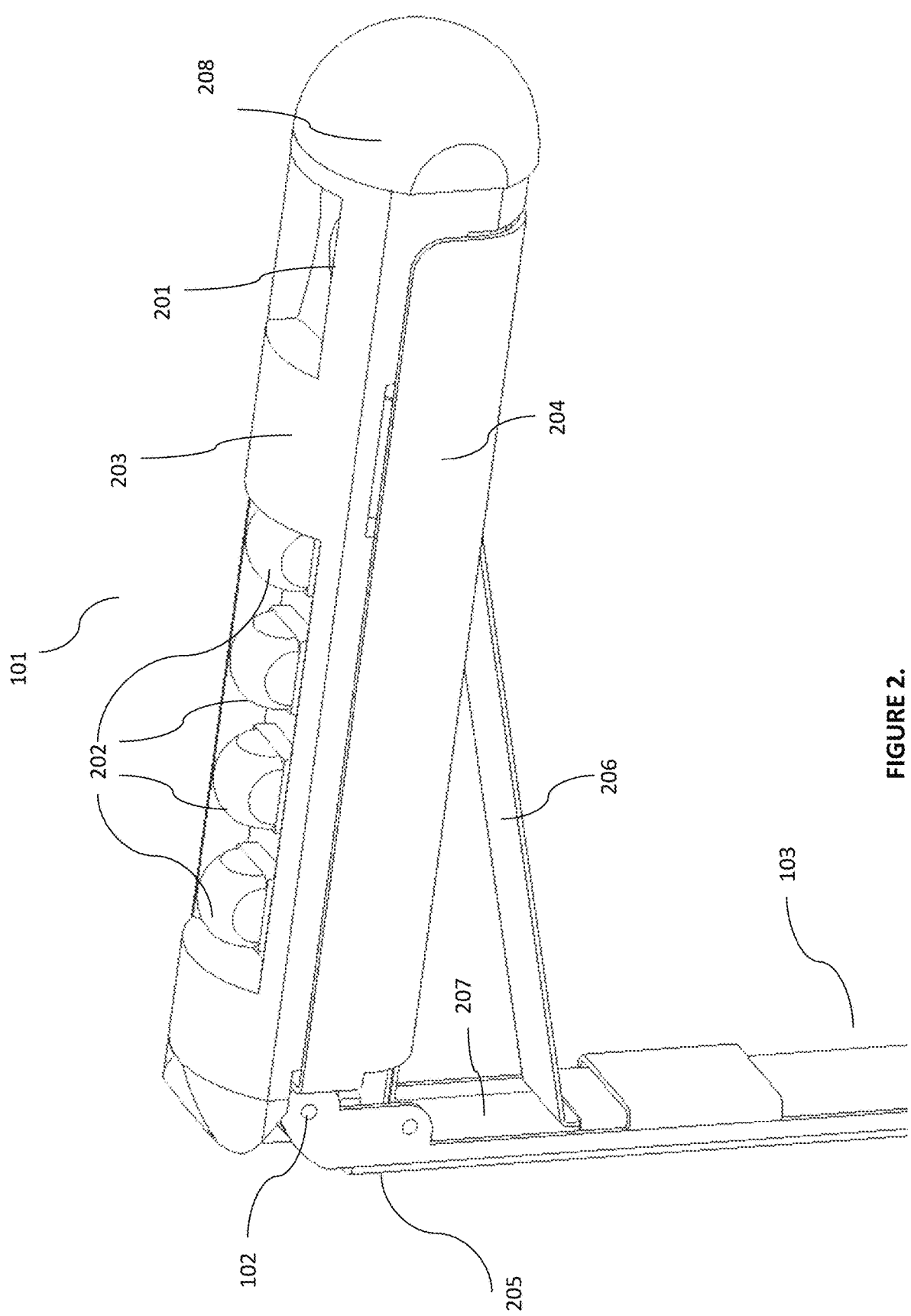
FIG. 2 illustrates an example side view of an endoscope at a distal section, where the endoscope is bent at about a 90 degree angle (deployed) at a joint, and used as a forward looking zero degree endoscope.
Figure 3A:
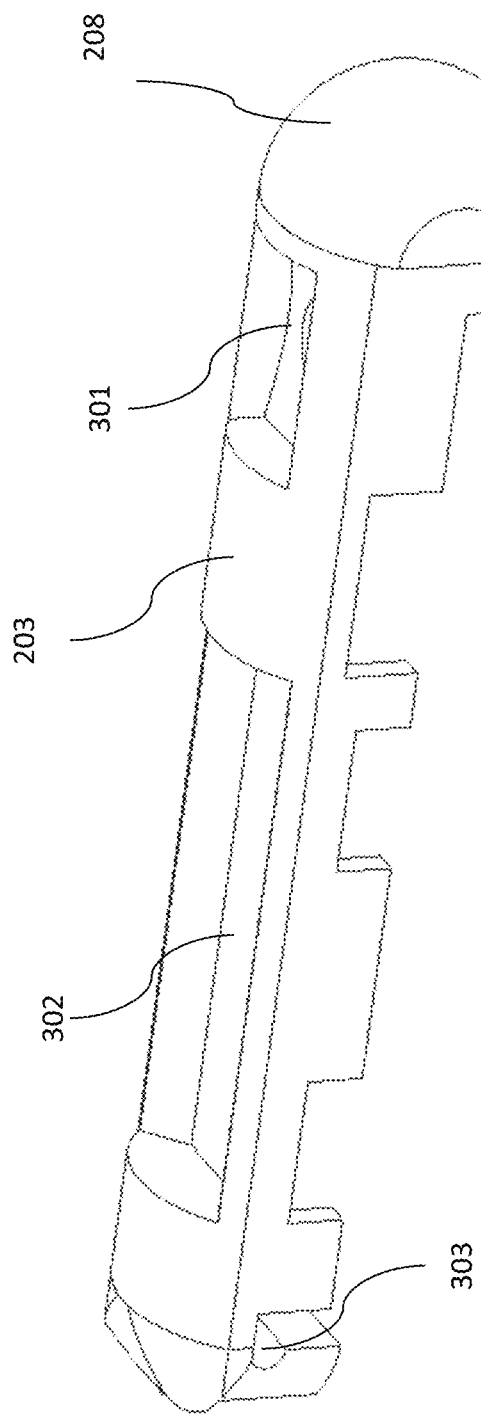
FIGS. 3a and 3b illustrate an example of possible distal section construction, incorporating electro-optics illumination light sources and a digital camera module, where a plastic component holder (FIG. 3a), positions the LED illuminators and the camera module, with a latch and lock mechanism at the distal end of the sheet metal body (FIG. 3b)

In some embodiments, the housing of distal section 101 is made of micro molded on-reactive materials, such as plastic, silicone, etc. or combination metal inserted plastic upper housing 203 (e.g., depicted in FIGS. 2, and 3a) of a specific shape, used to accurately position and align the light sources 202 and camera(s) 201 at a desired position and direction of view within distal section 101. The light sources 202 may be LED light sources. The housing of the distal section 101 of FIG. 2 may be cylindrical with a distal end 208 that is rounded for ease of insertion. In some embodiments, the distal section 101 is divided into upper housing 203 (e.g., micro molded plastic in FIG. 3a) and lower housing 204 (e.g., formed sheet metal in FIG. 3b), that are mated with locking features 305, for the upper housing 203 with latch mechanism 303 to latch onto the pivot pin 304 at distal joint 102, and to have the lower housing 204 to mate together in a lockable fashion to the molded plastic part (e.g., upper housing 203), keeping the camera(s) 201 and LED light sources 202 in fixed positions within the distal section 101 of the endoscope 100.

In some embodiments, the lower housing 204 can accommodate inclusion of a heat sink mechanism 306 under the light sources 202 to distribute the heat to the sheet metal body for better exposure to the surrounding air to aid in heat dissipation. Some of the heat transfer is also transferred to the imaging lenses 314 of the camera 201, to maintain fog free imaging during use. The upper housing 203 forms an aperture 301 for the camera 201, to be coupled and positioned with the camera 201 at a recess with respect to the to the distal section 101, surface, and a separate aperture 302 for the light sources 202 to be coupled to the distal section 101, with large enough opening to allow for a wide angle illumination. The optically opaque barrier between the separate apertures 301 and 302 (or window) in front of the recessed camera 201 and light sources 202, eliminates any cross talk and stray light issues between the light sources 202 and camera 201.

In some embodiments multiple LED or VCSEL light sources 202 with various spectral outputs can be used for spectral and fluorescence imaging. These light sources may have dome encapsulation over individual LEDs or VCSELs, to help light extraction and distribution of light in a specific manner. Individual dome encapsulation can be used on individual light sources (such as individually encapsulated LED light sources 202 in FIG. 3b), or multiple LED or VCSEL chips could have a common encapsulation, any combination of refractive or diffractive optics, or light pipe guiding and mixing mechanism over the multiple light sources.

Figure 4:
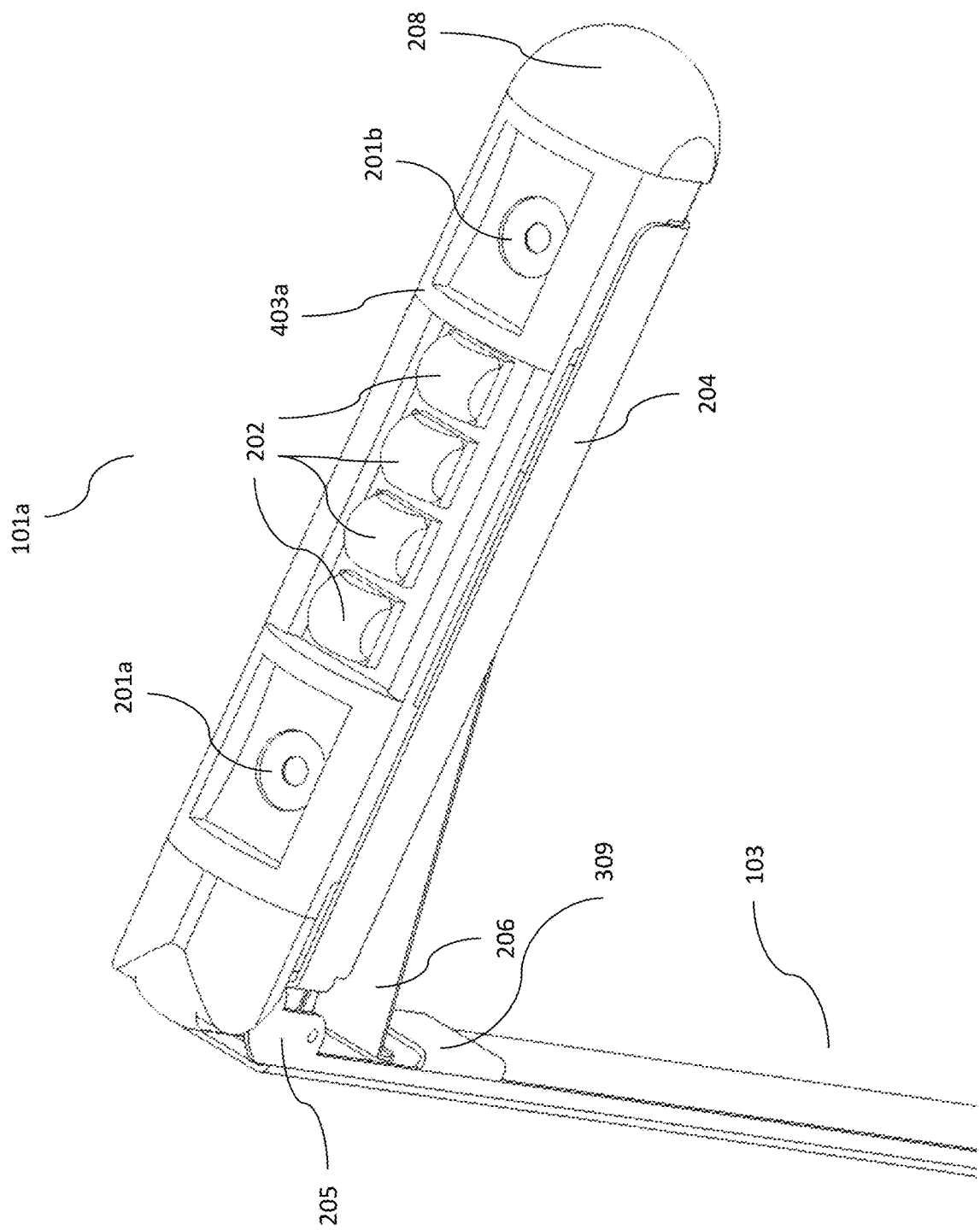
FIG. 4 illustrates a stereo endoscope, with dual camera heads.

In some embodiments, dual cameras 201a and 201b in FIG. 4, facing the same direction of view can be incorporated in an endoscope distal section 101a (FIG. 4), for stereoscopic imaging, or multiple cameras facing different directions can be employed for multi-view imaging. The position, direction of view and distance of the cameras can be fixed by the aperture and mechanical guiding features in the micro molded plastic or extruded plastic housing (e.g., upper housing 203), where individual cameras are made to point to a specific direction, and at a specific orientation and distance from one another.

The dual cameras 201a and 201b for a stereo vision deployable endoscope 100, can be conveniently positioned and spaced from one another, facing the side of the elongated distal section 101a (FIG. 4), instead of the traditional endoscope geometry where the endoscope has its camera(s) or input port facing the distal end of the endoscope, where space is very limited. Thus, the distal section 101 and distal section 101a cannot only accommodate larger, higher resolution, and higher sensitivity sensor sizes, but also larger and higher Numerical Aperture (NA) optics (lower f/#), providing higher resolution imaging with better light gathering capability.

In the case of the stereo endoscope of FIG. 4, the larger areas can also maintain a larger stereo separation along the long section of the elongated body of the distal section 101a, whereas this stereo separation distance is very limited in traditional stereo endoscopes, since both stereo camera vision ports have to be incorporated side to side, across the same small cross sectional area of the traditional tubular endoscope at the distal end. The larger stereo separation (inter-axial distance between the cameras 201a and 201b can be easily over 10 mm where as that of a traditional 10-11 mm diameter scope is usually less than 5 mm. This larger stereo separation allows for better 3D viewing at larger working distances.

A thin heat shrink with cut out opening for the camera 201 (201a, and 201b in FIG. 4), and light sources 202, can also be applied over the elongated distal section 101 (101a in FIG. 4), to hold tight the plastic body (e.g., upper housing 203) (or 403a in FIG. 4) with the lower housing 204, and/or over the stick body of the endoscope in the midsection 103 and proximal section 105 for protection. In some embodiments, a bulb like protective window made of thin molded plastic or glass could be placed on the camera housing of the camera 201 and/or the light sources 202 to act as an optical interface and window between the camera 201 and the light sources 202 where they are incorporated at the distal tip section of the endoscope 100. Alternatively if needed a very thin optically transparent heat shrink tube can act as the optical window over the apertures 301 and 302. A single (or multiple) bulb type or flat window with anti reflection coating, could act as a common (or separate) window for both the light sources 202 and the camera 201 in an alternate embodiment, where it can be built into or molded into the disposable endoscope 100 distal section (101) upper housing 203 at the apertures 302 and 301 of FIG. 3a.

Figure 3B:
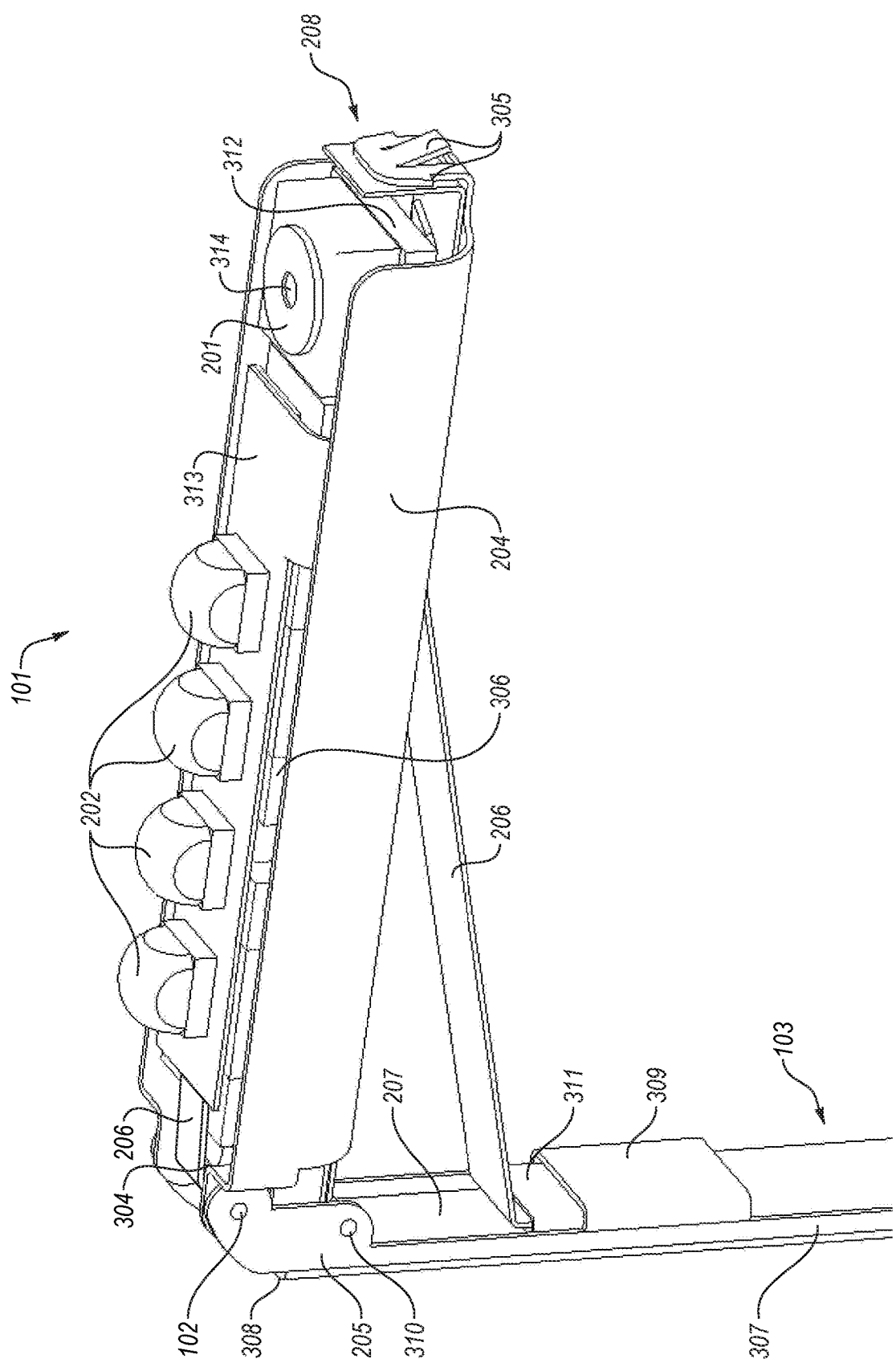
Figure 5:
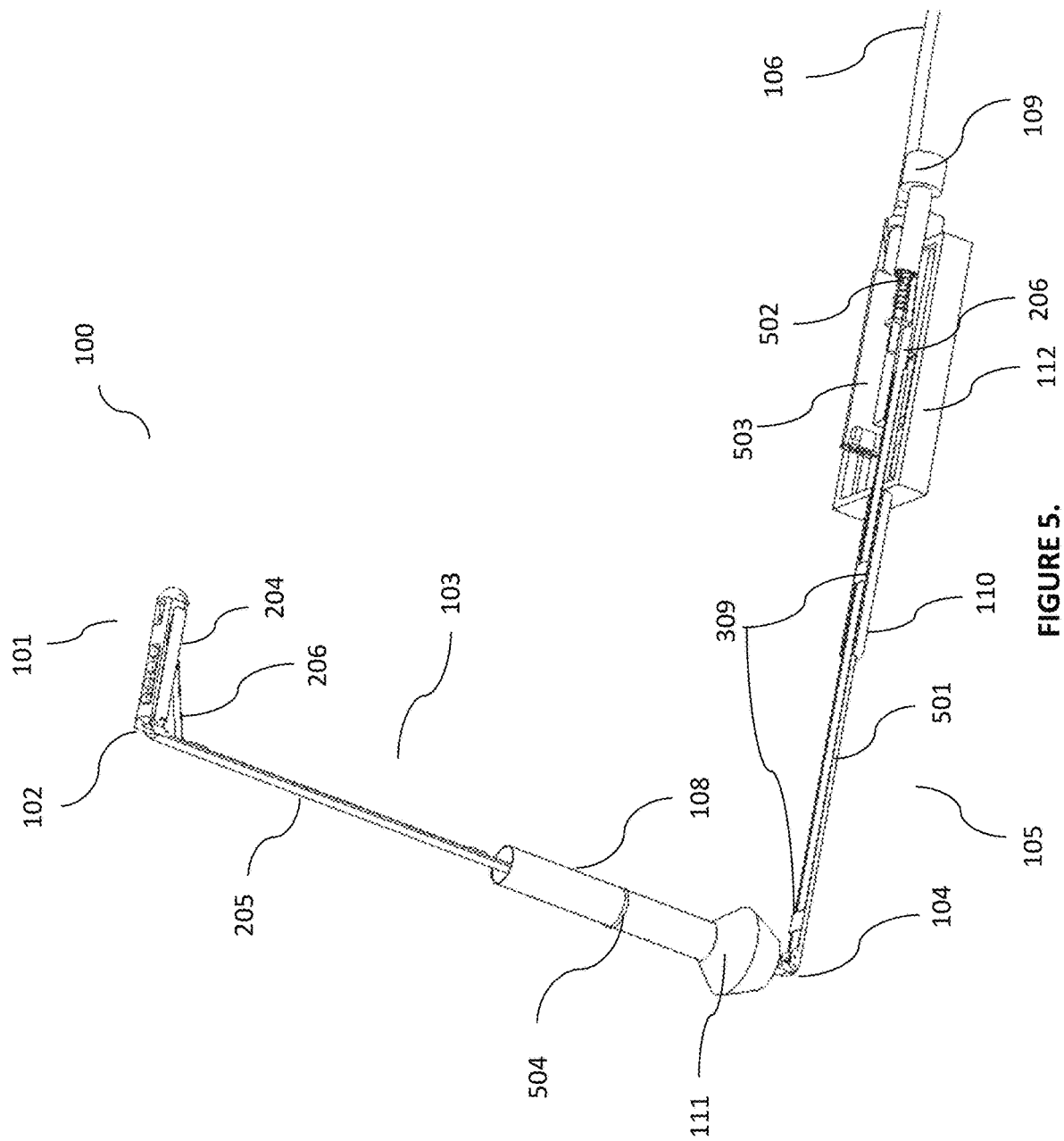
FIG. 5 illustrates the internal section of a proximal box, with a tension spring holding a deployment and articulation flat cable in position.

FIGS. 3b, 4 and 5 show the midsection 103 thin housing 205 coupled to the lower housing 204 of the distal section 101, at the pivot distal joint 102, with pivot pin 304, and the proximal section 105 passively coupled to the midsection 103 at the pivot proximal joint 104, using a similar pivot pin (not shown). In some embodiments, the lower housing 204 at the distal section 101, thin housing 205 in the midsection, and thin housing 501 in the proximal section, together form the multi jointed endoscope 100 body, securing flat electrical cables 207 and the flat actuation cable 206 along the endoscope body and through its articulating and bending joints, such as distal joint 102 and proximal joint 104. The multi-jointed endoscope 100 can be divided into more sections and pivot points along each section for further maneuverability and flexibility.

In some embodiments, the metal body (e.g., thin housing 205) in the midsection 103 of endoscope 100 may be made of metal (e.g., sheet metal) that is rigid or partially flexible where various bends, such as the side bends (307), cut outs (308) for effective range of bending, straps (e.g., sectional guides 309) to secure the cable routing mechanisms inside the thin housing 205, and stainless steel joining and strength pins. These pins, can be welded to the outer thin housing 205 at the joints (connecting sheet metal folds of thin housing 205), for example, at distal joint 102 by pivot pin 304, in FIG. 3b, to function as the joint hinge, where for example the sheet metal body folds and holes of lower housing 204 is free floating over the pivot pin 304, and thus made to easily rotate around the pivot pin 304. Alternatively or in addition these pins can be used to route and guide the flat cables for the endoscope 100 within the section or the joint, such as with pin 310, that strengthens the bending distal joint 102 as well as properly routing the flat electrical cables 207 above it, in FIG. 3b. The thin housing 205 along the midsection 103 of the endoscope 100, can be folded around the flat electrical cable 207 sides (as depicted as side bends 307 folds in FIG. 3b), with enough rigidity to make it easy for a user to grasp for inserting and withdrawing the endoscope 100 in and out of a port.

The sheet metal thin housing 205 in the midsection 103, or the sheet metal thin housing 501 in the proximal section 105, may also include sectional guides 309, (made of a sheet metal flap bent over and welded onto the sheet metal thin housing 205 and 501) for further protecting and directing the flat electrical and actuation cables 207 and 206 in the partially open sheet metal thin housing 205 and 501 of the endoscope 100, as depicted in FIGS. 3b through 6.

The flat electrical cables 207 and the deployment and articulation flat cable(s) such as flat actuation cable(s) 206, are secured properly inside the distal section 101 (secured at the illumination and camera modules in case of flat electrical cables 207, while the flat actuation cable 206 for articulation is secured to the inside of the metal lower housing 204 in the distal section 101, after passing through a cutout at the bottom of the sheet metal lower housing 204 (not shown). These thin flat electrical and actuation cables (207 and 206) can be routed differently through the distal bending joints of endoscope 100, and routed similarly through the endoscope midsection 103, or the proximal section 105.

For example in FIG. 3b, the sheet metal thin housing 205 with the pivot pin 304 at the distal joint 102, includes also pin 310 that directs and routes the flat electrical cables 207, above the pin 310 (but below the distal joint 102), where the bending of distal joint 102 (or hinge or pin) exerts the minimum change in tension in the electrical cables during articulation and deployment (due to the close proximity of guide pin 310 and distal joint 102), and whereas the flat actuation cable 206 is made to freely move below the guide pin 310 and the articulation and deployment distal joint 102, and thus with ability to form a triangular shape with respect to the deployed distal section 101 and endoscope midsection 103.

The sheet metal thin housing 205 at the midsection 103 and sheet metal thin housing 501, in the proximal section 105, together with the sectional guides 309 may also secure a smooth and low friction tubing 311 that is formed or pressed into the appropriate cross sectional form to accommodate the low friction manipulation of the deployment and articulation of the flat actuation cables 206, as they run through the endoscope midsection 103 and proximal section 105. The separate low friction guide channel (e.g., tubing 311), can be made of a flattened, thin walled PolyTetraFluoroEthylene (PTFE) tube, for example, which takes minimum space and yet provides a nearly frictionless motion of the deployment and articulation using the flat actuation cables 206 (and possibly free floating flat electrical cables 207) inside the sheet metal thin housing 205. The sheet metal thin housing 205 in the midsection 103 (and/or thin housing 501 in the proximal section 105) and tubing 311 can be housed further inside a thin heat shrink material for protection and further rigidity at the endoscope midsection 103 and proximal section 105.

In some embodiments, an extra flat actuation cable 206 for articulation can be routed over the pivot pin 304 (not shown), also routed inside a low friction (PTFE) guide channel such as tubing 311, where together the two top and bottom routed flat actuation cables 206 are used as deployment and un-deployment means with a small electromechanical articulation actuator, and further coupled to the proximal end control electronics and portable display and controller, for automatic articulation of endoscope by pulling each of the flat actuation cables 206 (not shown) that are secured at the distal section 101 of the endoscope 100.

Alternatively, in other embodiments, as passive means of deployment and active mechanical fine articulation, a single flat actuation cable 206 for deployment and articulation can be routed as described in FIG. 3b, where the flat actuation cable 206 is fixed inside sheet metal lower housing 204 (at the distal section 101), as described above, and placed under pre-set tension using a tension spring 502 that is housed inside the proximal housing 112 (depicted open in FIG. 5). In FIG. 5, the proximal sheet metal thin housing 501 and flat actuation cables 206 for deployment and articulation, are coupled to the articulation and deployment tension spring 502, after the passive bending proximal joint 104 (or hinge or pin), inside the proximal housing 112. The flat actuation cable 206 for articulation and deployment, secured and placed under tension by the tension spring 502 is configured to be under various tension (adjustable by the knob 109) allowing the endoscope to bend from 0 degrees to 90 degrees, and look both at the side of the organ as well as behind the organ. In some embodiments the endoscope 100 can be bent to any angle, such as, for example 30 degrees, 45 degrees, 70 degrees, while it is being used to operate or observe within the body cavity, without having to take it out of the body. In some embodiment, the articulation and deployment spring mechanism is configured to allow the endoscope to bend up to 180 degrees onto itself, or bend in the opposite direction to look back onto its insertion position.

Articulating and/or deployable embodiments are possible for effective illumination and imaging of a surgical site at various angles, without the need to change to a new angled endoscope. Although the camera 201 and light sources 202 can be on the same plane as the endoscope midsection 103 that is inserted into the port and cavity, in some embodiments, the camera 201 and the light sources 202 can be articulated from an insertion position, or deployed from a collapsed profile before use (pointing to various directions). In some embodiments, the camera 201 and the light sources 202 are held within a close profile of the insertion body to an operational position where they are conveniently expanded axially, deployed and articulated, pointing to an object of interest. In operational position, the illumination light from the light sources 202, as well as the imaging FOV of the camera 201, can be directed to the surgical site from beyond the endoscope body, or behind a body organ increasing the functionality of the surgical device.

Alternatively, in other embodiments, multiple cameras can be incorporated into the articulating and deployable endoscope 100 to provide multi-view imaging (with cameras concurrently looking at different or even opposite front and back viewing directions), or as stereoscopic or 3D visualization (with two cameras directed as left and right eye for the 3D vision system. Multiple of various wavelength LEDs and VCSELs can be used at the distal end of the endoscope to perform Spectral imaging, or detect fluorescent dye inside the veins or, to induce bio-fluorescence in the tissue and provide imaging of based on its fluorescence characteristics.

With the extra space provided at the elongated distal section 101 of the endoscope 100, where cameras face the side of the elongated section instead of the circular cross section of the endoscope 100, electromechanical means of autofocus and/or zooming can be incorporated on the camera lenses where the distance between the camera lenses and/or the lenses and the camera sensor can be adjusted for fine focusing or zooming of the camera. The electromechanical means for autofocus and zooming can be controlled via the same flat electrical cables 207 (or additional flat cables 207) by the control and display electronics similar to USB cameras equipped with autofocus mechanism. Similarly Liquid Lenses can be mounted on top of the camera lenses and electronically controlled through the same or more flat electrical cables 207, to perform autofocus and/or eliminate hand tremor or any vibrations of the endoscope that could cause blurring of the image.

In some embodiments, the flat electrical cables 207 as well as the flat actuation cable(s) 206 for deployment and articulation, are thin Flexible Printed Circuit (FPC) cables. The advantage of FPC cables is that they are flat and take up minimal space, yet are very strong and able to withstand substantial pull force without change in length. For example, the FPC cables with only 3 mm width and 150 µm thickness can be easily used not only as multi conductor, high speed communication lines, but also as strong and low friction flat cables under continuous tension for the purpose of deployment and articulation. Other cable designs are possible, such as Flat Flexible Cable (FFC), with Teflon type jacket.

In a multi-cable articulation scheme, dual flat actuation cables 206 can be the same cables as the flat electrical cables 207 that could be positioned above and below the distal pivot pin 304, and secured above and below the distal section 101, on the opposite sides of the articulation and deployment distal joint 102. The flat actuation cables 206 can serve as actuators for the articulation and deployment of the distal joint 102. For example, pulling one cable causes the endoscope to open and bend at an angle (e.g. 30, 60, or 90 degrees). Pulling the other cable causes the endoscope to close and form a tubular geometry for insertion into the body cavity.

In addition, the flat electrical cables 207 (or flat actuation cables 206) provide electrical current to the camera 201 and the light sources 202, control signals to the camera 201, and transmit MIPI signals from the camera 201 to a control electronic board (e.g., 503 of FIG. 5) at the proximal section 105 of the endoscope 100 and a portable display and controller (not shown), connected through USB cable 106. The control electronic board 503 inside the proximal housing 112 (FIG. 5), with Digital Signal Processing (DSP) chip, which is discussed in greater detail below, converts the MIPI signal to a USB Video Class (UVC) format for interfacing with off-the-shelf computers connected to the USB cable 106 of the endoscope The flat actuation cables 206 may be partially or sectionally encased in tubing 311 of FIG. 3b. The tubing 311 may be made from a variety of materials as long as the tubing 311 has a low coefficient of friction and can be drawn with a very thin wall to save space in the endoscope body. For example, the tubing 311 may be a thin walled (PTFE) tubing of wall thickness 0.01" or less. The tubing 311 may also be formed into the appropriate crescent shape to mate the port internal wall nicely, or squeezed into flat or oval shape, made from a round thin wall tube. Low profile FFC or FPC cable connectors can connect the flat electrical cables 207 to flexible circuitry 313 or a small and thin rigid Printed Circuit Board (PCB) 312, which are used to mount the camera 201 and the light sources 202 with appropriate support electronics mounted on the same flex circuitry 313 and rigid PCB 312, of FIG. 3b.

The camera 201 captures images inside the cavity. The camera 201 may be a digital camera that uses a Complementary Metal-Oxide Semiconductor (CMOS) sensor for converting light into electrons. Multiple high resolution digital cameras can be connected through multiple FFC flat electrical cables 207 for stereo or multi-directional viewing, where all the cameras are connected through a high bandwidth USB HUB in the proximal housing 112 or connected to the Display and Controller through multiple USB cable 106. A high bandwidth, electrically isolated power USB 3.0 cable or USB 3.1 optical cable can make the connection at the proximal housing 112, instead of the USB cable 106, where multiple high resolution cameras are concurrently displaying a 2D or 3D image with fast frame rate through a USB hub, taking advantage of the high bandwidth of a single optical USB cable.

To allow successful leak free insufflation of the body during operation, a thin flexible (tubular) insufflation membrane 107 is permanently attached to the midsection 103 of the multi jointed endoscope 100 (FIG. 1). As depicted in FIG. 1, the thin flexible insufflation membrane 107 is open towards its distal side, but collapsed and securely mounted closed, at the proximal side, to the midsection 103 of the endoscope 100.

Figure 6:
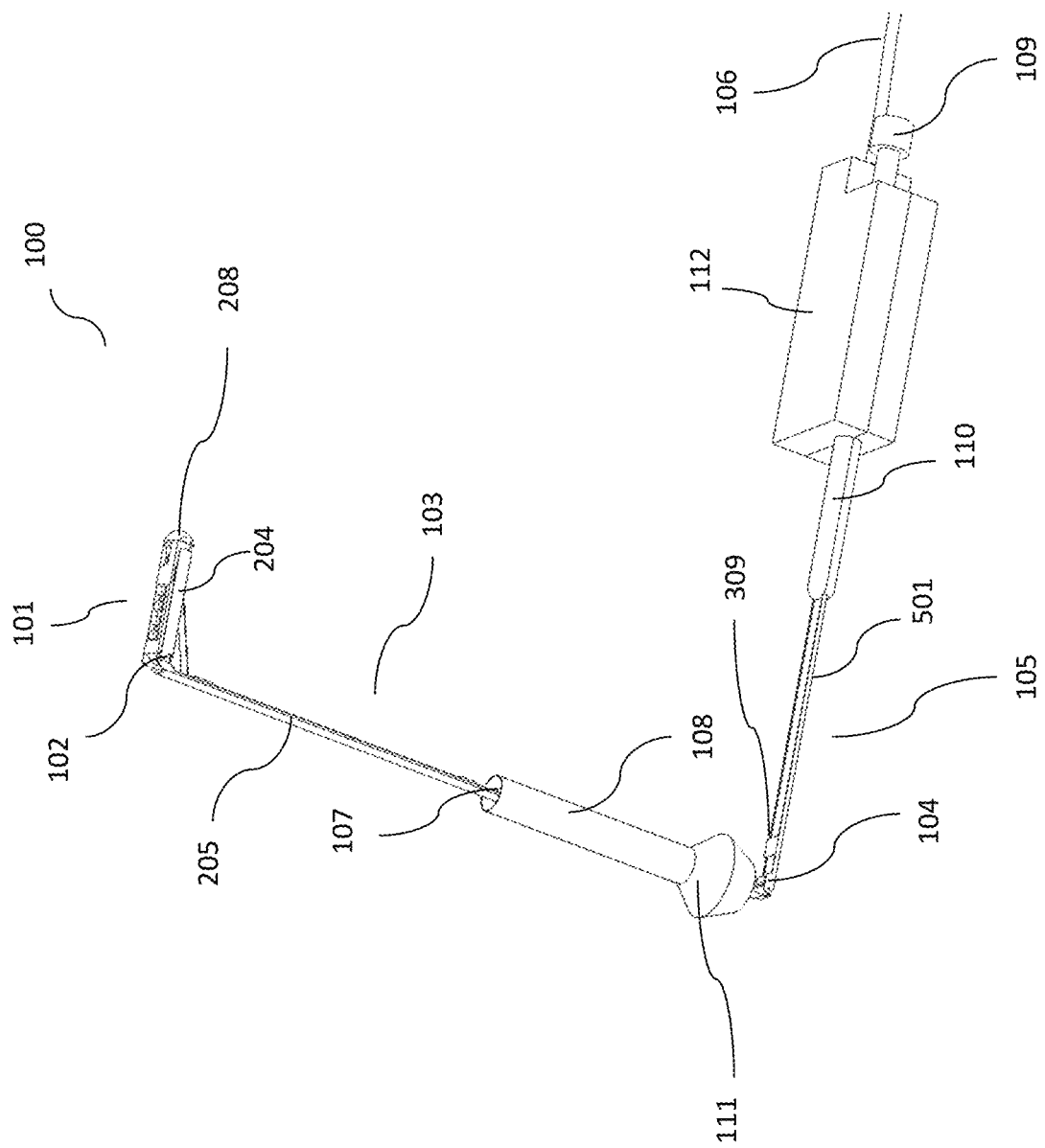

Before the insertion of the endoscope 100 into the port, a rigid or semi-rigid insertion tube (introducing guide) 108, with a rigid enlarged proximal end 111, is moved from its proximal resting position 110, to cover the thin flexible insufflation membrane 107 of the endoscope 100, as depicted in FIGS. 5 and 6. The enlarged proximal end 111 of the rigid insertion tube 108, made larger than the port opening, acts as a plug for the port during insertion, properly positioning the insertion tube 108 protecting the thin flexible insufflation membrane 107, allowing it to stretch and pass through the port insufflation membrane or opening at position 504, as further described below and depicted in FIG. 8.

In a passive embodiment of the deployment, the tension spring 502 of FIG. 5, could be initially set and fixed in place inside the proximal housing 112, with the distal section 101 of endoscope 100 in a predetermined deployed angle with respect to the midsection 103 of the endoscope that will be inside a port. For example, in FIG. 5, the tension spring 502 and knob 109 are initially set (and fixed in the proximal housing 112) so that distal section 101 is at right angle with the midsection 103 of the endoscope (with all electrical and deployment and articulation cables routed and passing through the distal joint 102, as described above in FIG. 4, and though the passive bending proximal joint 104 in the same manner).

Figure 7:
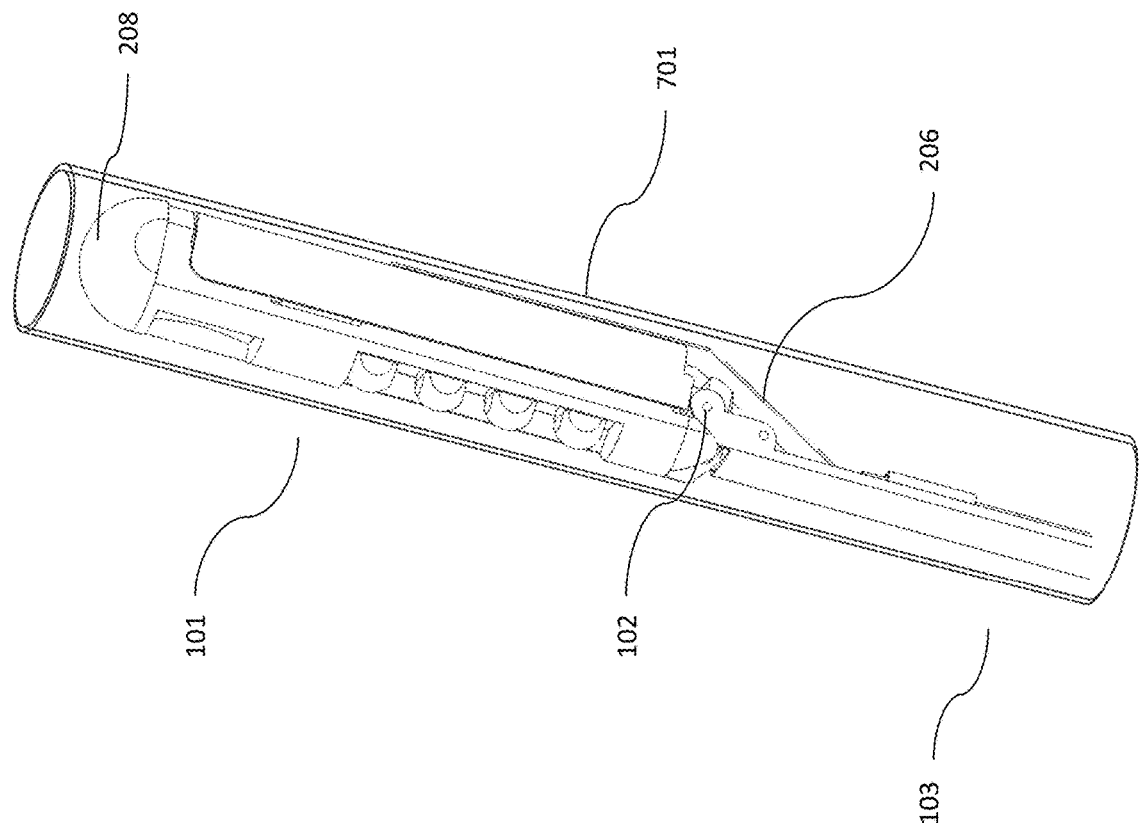
FIG. 7 illustrates an example perspective view of an endoscope, near a distal joint, made into a tubular geometry during insertion through a port, where the endoscope distal head section is straightened with respect to the midsection of the endoscope, at the joint, as it is inserted into the port, pulling on an actuation cable close to the endoscope body, applying further tension to a tension spring that holds the actuation cable at the proximal section of the endoscope.

FIG. 6, depicts the insertion of the endoscope 100 into the port before insertion into the port. To insert the endoscope 100 into the port from the rounded distal end 208, with the insertion tube 108 positioned and held over the thin flexible insufflation membrane 107, the distal section 101 of the endoscope 100 can be straightened at distal joint 102 by the user, so the distal section 101 is now along the midsection 103 of the endoscope, as depicted in FIG. 7 (which was initially set at right angle position by the tension spring 502 as shown in FIG. 6). The endoscope 100 is inserted into port 701 of FIG. 7, with the rounded distal end 208 opening the port 701 insufflation membrane(s) for the endoscope 100 to pass (not shown). In the straight insertion position of the endoscope 100 illustrated in FIG. 7, the deployment flat actuation cable 206 collapses (from the triangular position depicted in FIG. 6), onto the endoscope body at the distal joint 102 in FIG. 7, pulling further on the flat actuation cable 206, and applying more tension in the proximal tension spring 502 of FIG. 5.

Figure 8:
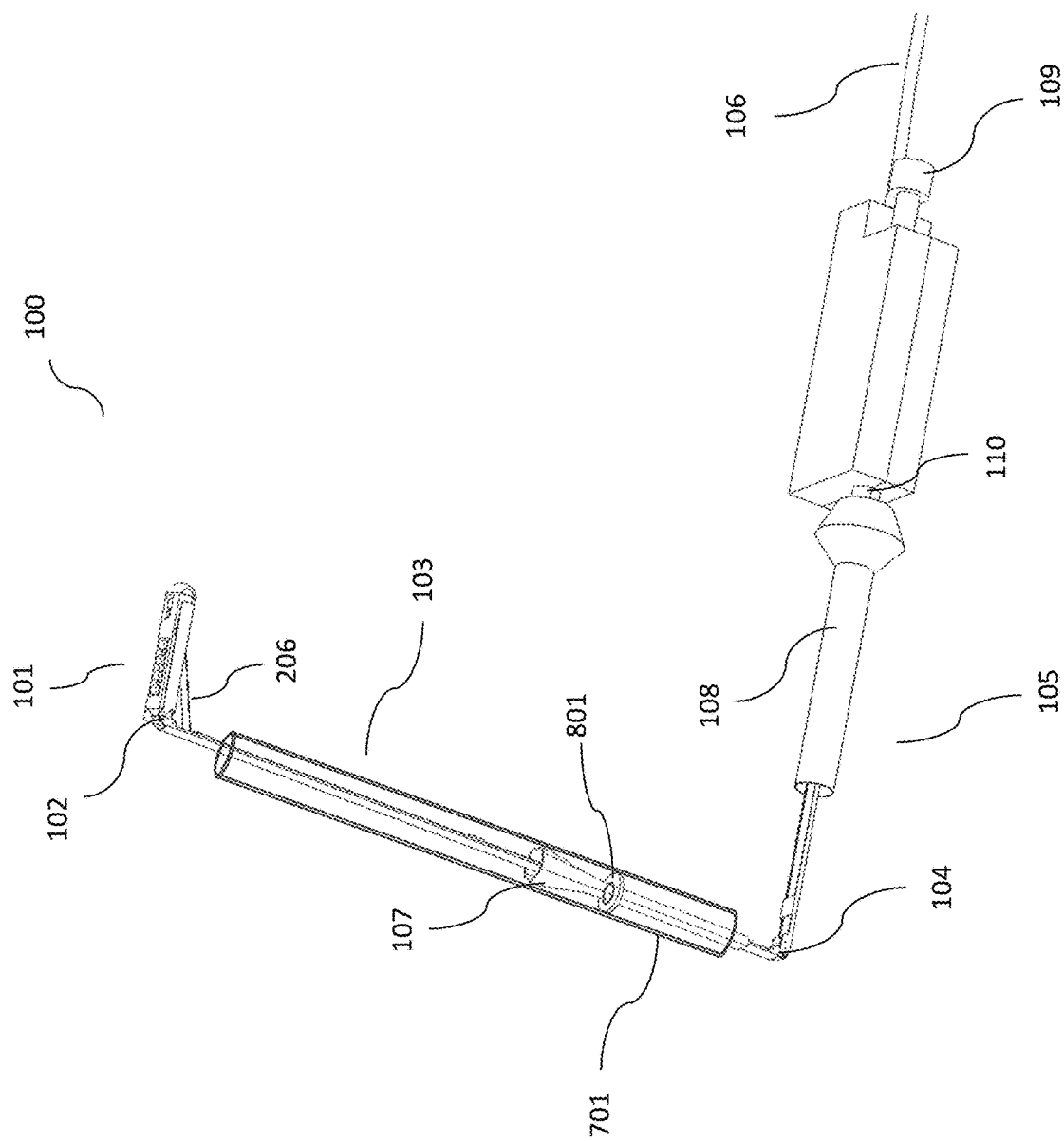
FIG. 8 illustrates the deployment of a distal section, at the distal tip of a port, as an actuation cable reverts back to an initial tension setting, passively bending the endoscope distal tip section to a deployed position (about 90 deg.) at the distal end of the endoscope.

Once the distal section 101 has safely cleared the distal end of the port 701, the tension spring 502 pulls back on the flat actuation cable 206, bringing the distal section 101 back to the right angle position set by the tension spring 502 initially in the proximal housing 112 (FIG. 5). At this point, the insertion tube 108 is positioned within the port 701 of FIG. 7, with the insufflation membrane opening of the port, at position 504 of the insertion tube 108 (FIG. 5). The insertion tube 108 is then removed from the endoscope midsection 103 inside the port, and placed back on its original proximal resting position 110 (as in FIG. 1), by unbending proximal joint 104 and letting it bend back again. This removal of insertion tube 108, exposes the thin flexible insufflation membrane 107 to the port insufflation membrane 801 of port 701, as illustrated in FIG. 8, where the air from inside of the body inflates the thin flexible insufflation membrane 107 like a skirt providing an air tight seal around the endoscope midsection 103 of endoscope 100 at port insufflation membrane 801 of the port 701. To change the insertion length of the endoscope body inside the port, the insertion tube 108 can be reinserted over the partially inflated thin flexible insufflation membrane 107 to open the port insufflation membrane 801 once again, and to safely reposition the endoscope midsection 103 at a new position within the port 701.

Once the endoscope 100 is deployed inside the body, other devices (illustrated as device 904 for simplicity in FIG. 9), can be inserted through the same port 701 pushing the midsection 103 of the endoscope to the side wall of the port 701, where the new device 904 body collectively with the thin flexible insufflation membrane 107, can now stretch and provide the insufflation seal inside the port insufflation membrane 801 (not shown). The device 904 may be a surgical device for example for manipulating and operating on an organ inside the cavity, or a separate endoscope.

Figure 9:
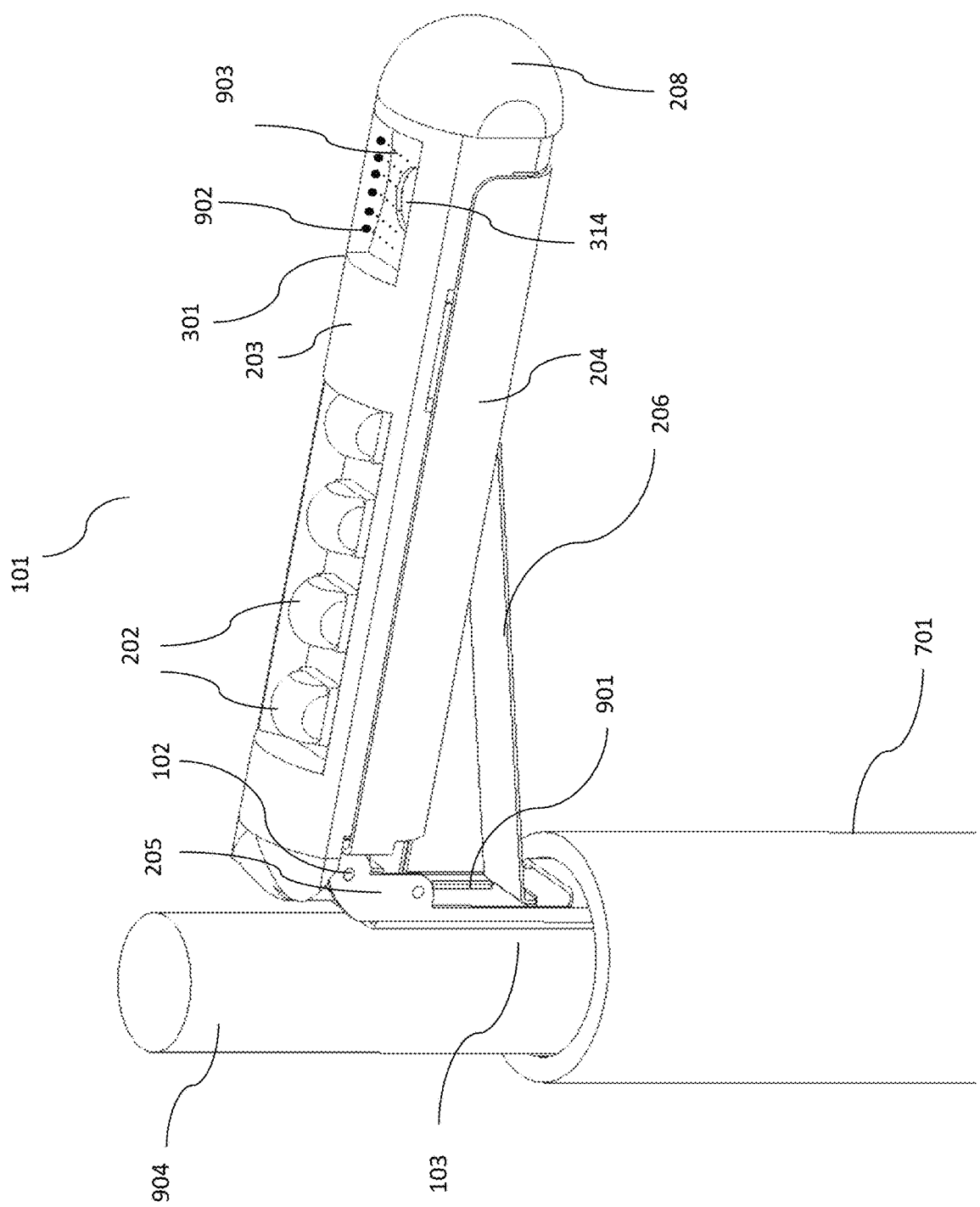
FIG. 9 illustrates an example side view of an endoscope system that illustrates a tubing and air jet outlets for forming an air jet above and over the camera optics of a camera.

FIG. 9 further illustrates an example side view of an endoscope 100 where an air supply micro-tubing 901 is routed along the length of the endoscope (e.g., through sections 105, 103 and 101 of the multi jointed endoscope 100) with high pressure air jet nozzle termination 902, for projecting an air jet 903 directly in front of the camera 201, thus forming an air shield to prevent liquid and blood from obscuring the view of the camera (not shown). As a result, the air jet allows imaging rays to pass through the camera aperture 301 uninterrupted by any index of refraction change, and be sensed by the camera 201 through imaging lenses 314.

The camera 201 includes one or more imaging lenses 314 or optical filters, and an image sensor (not shown). In some embodiments, a thin clear optical window, is also provided to enclose the imaging lenses 314 and image sensor within the camera housing that is mounted on rigid PCB 312. The clear optical window of the camera could have micro holes similar to air jet nozzle termination 902, built in, where the air jet provided by micro tubing 901 can be routed to flow out from inside the camera window housing, and the out flowing air jet through the micro holes in the clear optical window to keep the optical window clear of any liquid. Although flexible circuitry 313 is illustrated for the LED light sources 202, and rigid PCB 312 for the camera 201 in FIG. 3b, light sources 202 and cameras 201 may be mounted on the same or separate rigid or flexible processing board, a combination of a rigid and flexible electronic processing board, or flexible electronic board with separate thin metal backing for the protection of individual components.

The light sources 202 can include monochromatic, polychromatic visible, Ultra Violet (UV), and/or Infra-Red (IR) solid state light sources such as high power Light Emitting Diodes (LEDs) and/or VCSELs for illuminating the cavity for the camera 201 to capture an image in specific range of wavelengths, or combination of wavelengths.

In FIG. 9, the camera 201 and the light sources 202 housed in distal section 101 and illustrated as being attached to the distal section of the multi jointed endoscope 100. Alternatively the endoscope distal section 101 (e.g., containing the vision system) may be attached to (via one or more bending distal joints 102), to the midsection 103 of the endoscope, where the midsection 103 may be built into a rigid medical device (1001a), flexible medical device (1001b), partially flexible, or expandable medical devices of FIGS. 10a and 10b, or within the wall of an anatomically shaped, hollow access device 1101, such as a flexible catheter, or open port (FIG. 11), wherein, the midsection 103 may have a thin body. In such integrated embodiments, the flexible flat actuation cables 206 and flat electrical cables 207 can be routed straight or in a spiral fashion with the body or wall of medical device 1001b or hollow access device 1101. The body of the medical device 1001a, medical device 1001b, and hollow access device 1101 can be permanently shaped to receive a rigid midsection 103 of the endoscope, or provide through holes to independently route the flexible flat actuation cables 206 and flat electrical cables 207 in the body of flexible or malleable medical device 1001b, or hollow access device 1101 (such as an articulating flexible catheter), where the distal section 101 is pre-procedure shaped (bent to desired angle) or actively manipulated during procedure to point to the desired FOV. The midsection 103 may have a thin body.

Figure 10A:
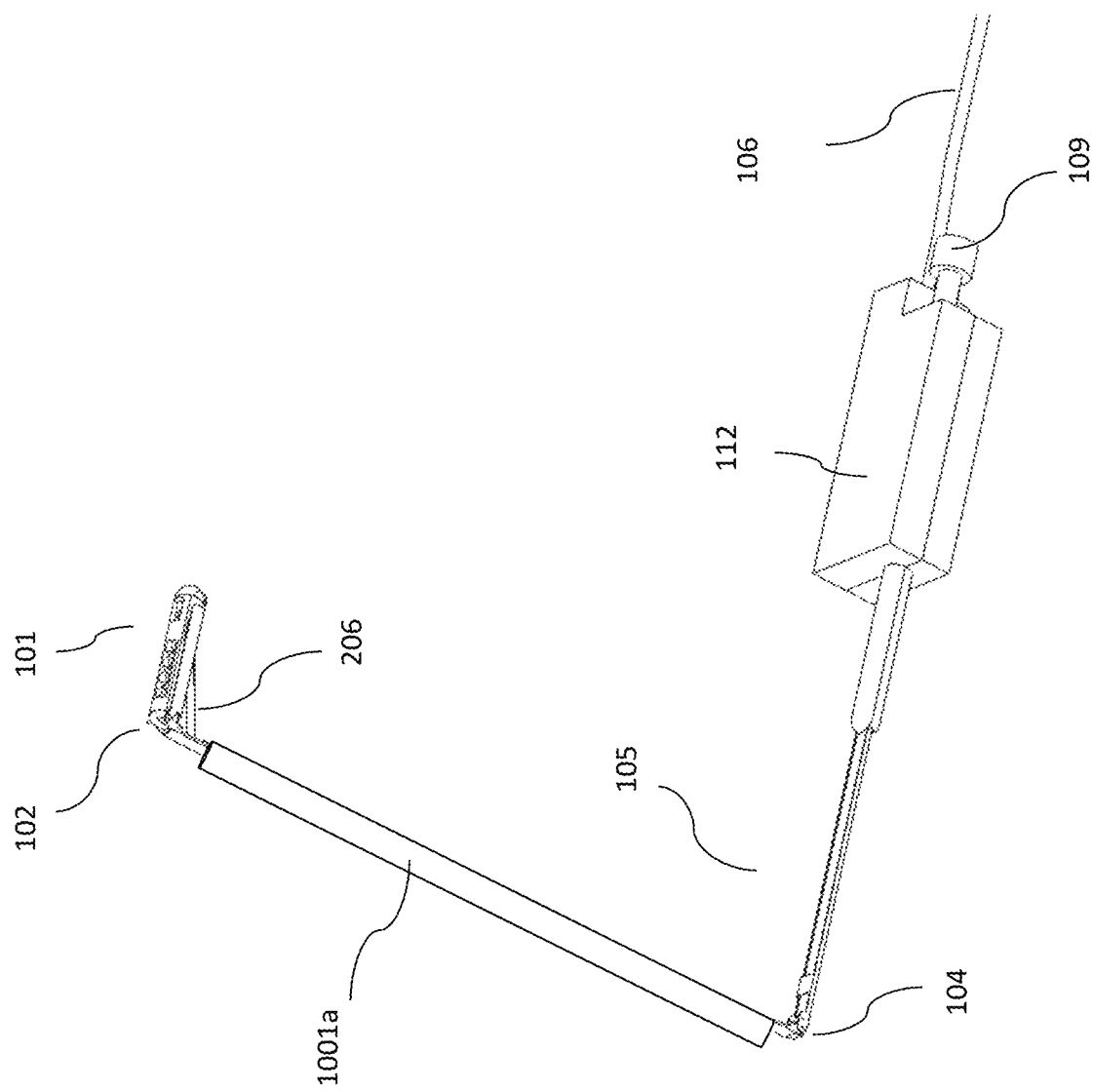
FIG. 10a illustrates the thin midsection of the endoscope integrated into the body of another rigid tubular device.
Figure 10B:
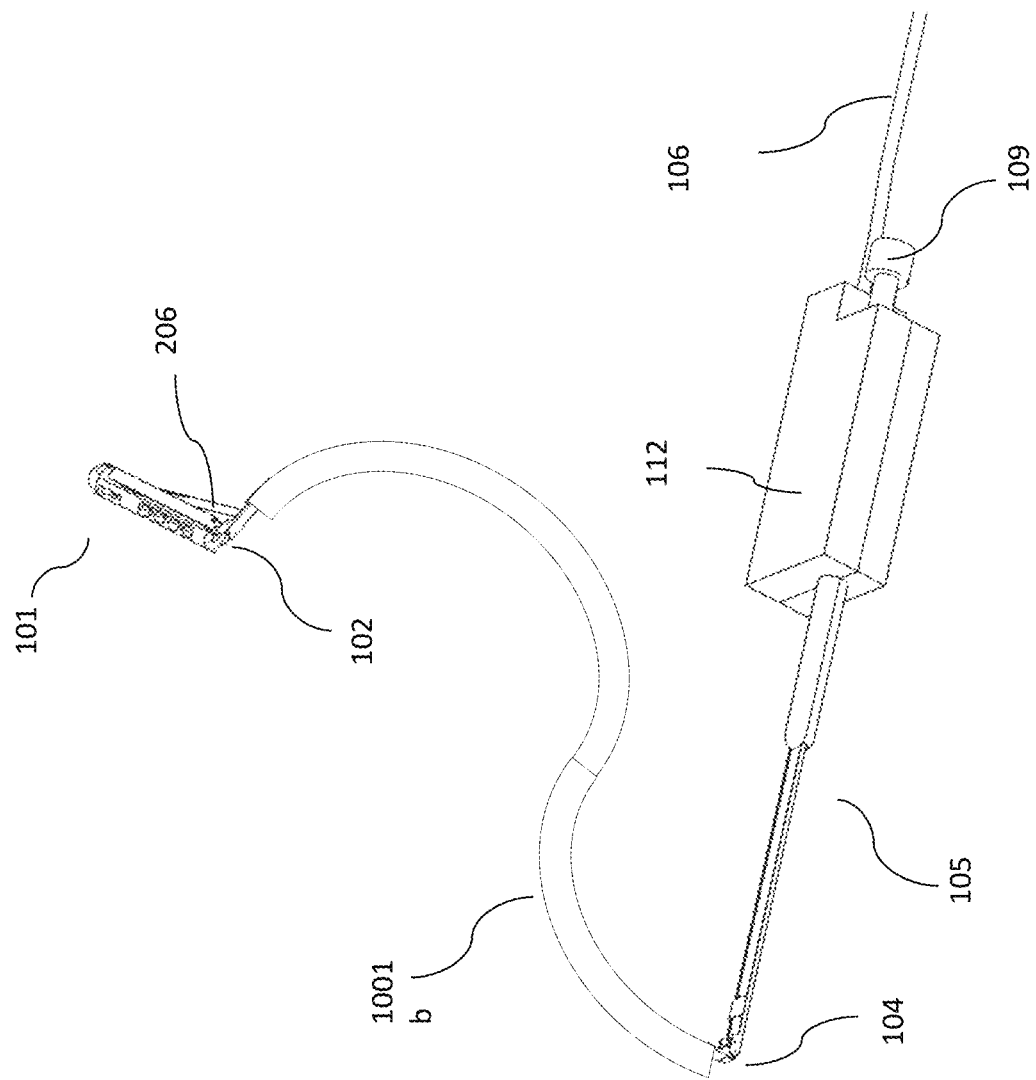
FIG. 10b illustrates the thin midsection of the endoscope made longer and integrated into the body of a flexible, partially flexible, or articulating tubular device.
Figure 11:
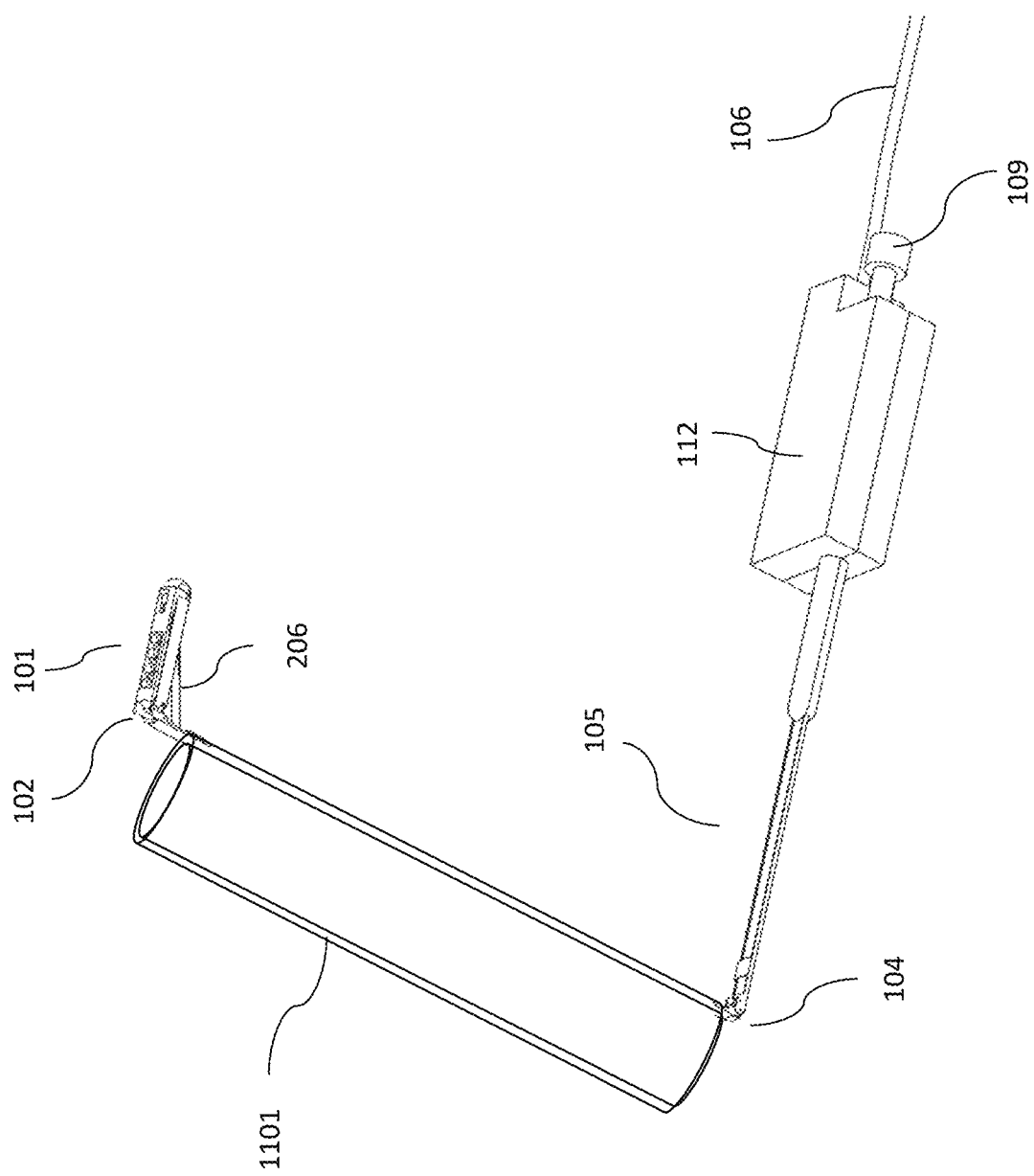
FIG. 11 illustrates the thin midsection of endoscope integrated into the wall of a hollow rigid port or a flexible hollow port or catheter.

The deployable endoscope section is inserted into the body, with the distal section 101 straight in front of the medical device 1001a, medical device 1001b, or hollow access device 1101 in FIGS. 10a-b and 11, and then subsequently deployed and articulated using the flat actuation cable(s) 206 that can be routed through a smooth open channel within the body of the medical device 1001a, 1001b, or hollow access device 1101, along with the same deployment and articulation flat cables carrying the electrical and power signals or separate flat electrical cables such as 207, routed through the same or other channels in the medical device or port, connected to the housing of the proximal section 105 of the multi jointed endoscope.

Figure 12:
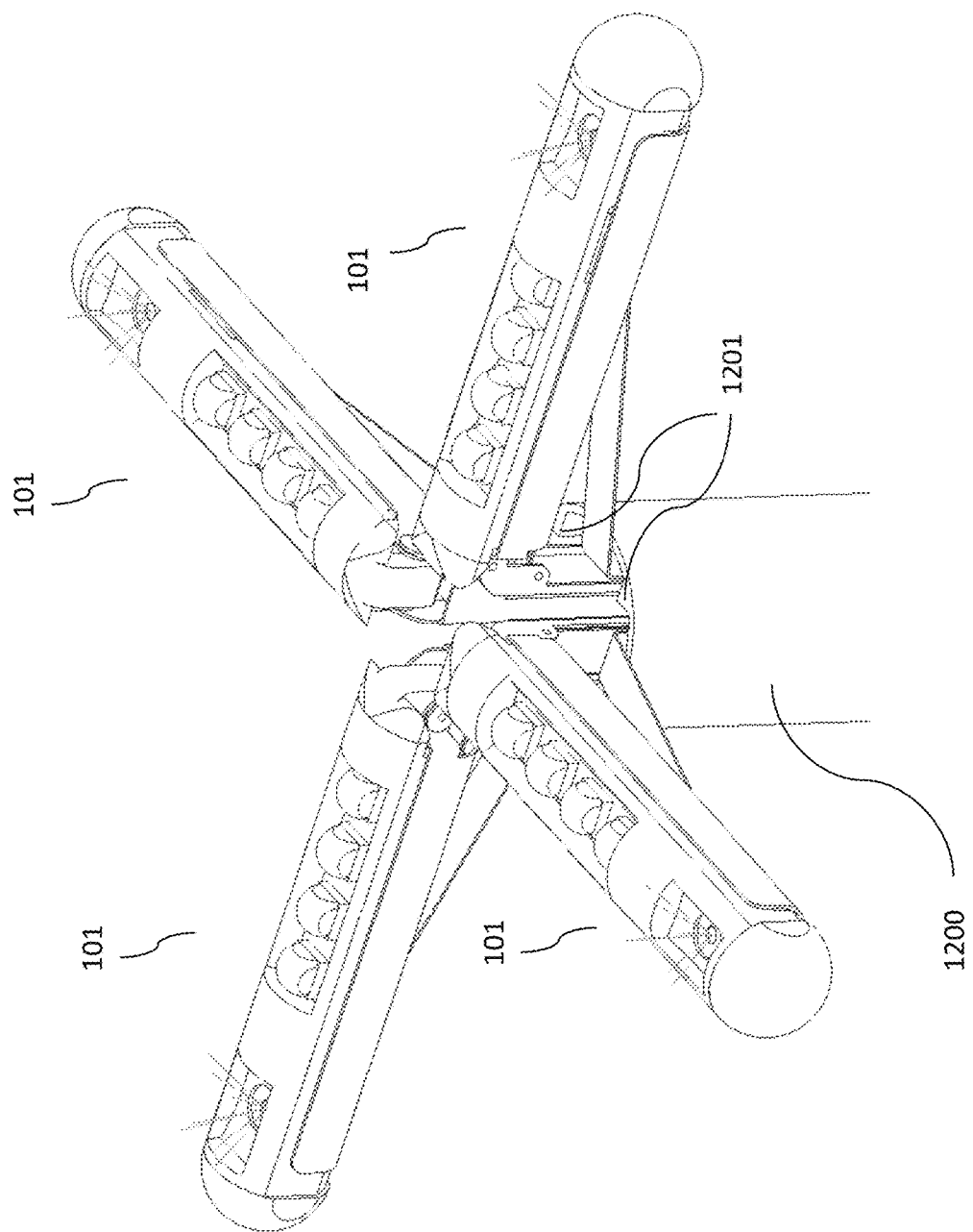
FIG. 12 illustrates 4 multi jointed deployable and articulating endoscopes, deployed at the distal tip of a single access port.

In these configurations the midsection 103 of the deployable and articulating endoscope 100 in FIG. 9, is permanently built into the distal end of the device 904 or the port 701 (not shown). Alternatively device 904 or port 701 of FIG. 9 can have appropriate space or grooves built into their elongated body and made to receive the midsection 103 of the multi jointed endoscope 100, thereby keeping the orientation of the endoscope fixed with respect to the device 904 or port 701. Multiple spaces or grooves can be built into the same device 904 or port 701 at various or opposite sides, where multiple endoscopes 100 can be inserted and held in fixed position with respect to device 904 or port 701, all inside the same port 701. The multiple endoscopes 100 can be inserted one at a time and deployed at distal joint 102 through the same port 701 in opposite directions (opposite sides of the port distal opening), or in the four quadrants at the port 701 distal end for example, where the proximal joint 104 of each of the endoscopes allows the proximal section 105 of each endoscope to bend similarly in opposite directions from one another at the proximal side of port 701 (out of the way of the separate device 904 inserted through the same port 701). The multiple endoscopes can provide views from multiple independent directions, or the image from the multiple endoscopes can be stitched together to provide a hyper FOV of inside the body. FIG. 12 illustrates 4 deployable and articulating endoscopes 100 each with its own independent illumination and camera modules within the distal section 101, deployed at the distal tip of access port 1200 in four opposing quadrants, where each endoscope is aligned and housed in its mating groove 1201 after insertion and deployment at the distal tip of access port 1200.

The light sources 202 or individual light source 202 and its drive electronics can be connected to the same proximal control electronic board 503 or have its own flexible circuitry or flat electrical cable 207 connection, receiving power directly from the USB cable 106, possibly as an individually controlled illumination source through a hub, where it is turned on and off as individual USB illuminator. The flexible circuitry, also known as a flex circuit, can be used to provide power and control signals to the camera 201 and light sources 202 and to transmit serialized imaging signals to a portable control and display unit, where part of the USB cable 106 can be enclosed along the flexible or rigid body of the disposable endoscope 100, and part of the USB cable 106 can be outside the endoscope 100, where the entire USB cable 106, can be disposable along with the endoscope 100.

The portable control and display unit generally includes a display screen, housing, illumination and imaging control electronics, image processing electronics, and/or a power supply, such as a battery. Such compact vision and illumination modules (cameras 201, 201a and 201b, and light sources 202) used in the distal section 101 of endoscope 100, without means of power or control electronics of their own, can be made in a compact and low cost form to make it easily introduced into the body within a small diameter disposable housing, by itself or introduced into the body as means of access for standard medical devices, where they can be removed and disposed of after a single use. Standard low cost and proven LED light sources 202 and digital CMOS sensor and limited electronics that normally would not fit within the distal tip of a traditional endoscope, can be used on the small flexible or rigid electronic boards at the elongated distal section 101 of the endoscope 100, with the main electrical components housed on a small control electronic board 503 in the proximal section 105 of the endoscope. Highly sensitive and high resolution digital sensors with integrated System On the Chip (SOC) electronics can convert the parallel digital video signals of the sensor to MIPI output from the high resolution digital sensor. The MIPI signals can be transferred along the length of the endoscope 100 using low cost and very thin, low profile FPC or FFC cables for over 1 meter length if need be, without the need for any electrical shielding, in case of a long flexible endoscope 100 or use with a long flexible catheter (such as medical device 1001b in FIG. 10b) for visualization inside body's natural orifices. Low cost proximal digital signal processing (DSP) chip, in the proximal section 105 of the endoscope, for example can convert the MIPI signal to high speed USB (Universal Serial Bus) video class camera signals (UVC, or USB Video Class format), similar to commonplace USB Web cameras. Alternatively the endoscope can send (MIPI) enabled serialized digital sensor outputs to a MIPI enabled portable display and controller directly without conversion to USB format, and using FFC cables instead. MIPI or USB signals can also be converted in the proximal control electronic board 503 to DVI or HDMI format video outputs for variety of other devices, or streamed over Wi-Fi, functioning as a network camera.

In some embodiments, a separate flexible USB cable 106 communicatively couples the portable control and display unit to the camera(s) 201 and light source(s) 202, as individual USB devices to communicate power and control signals, as well as serialized high speed digital video imaging signals in the UVC format between the portable control and display unit and the camera(s) 201 and light source(s) 202. As such, the flexible circuitry (USB cable 106) can use, power isolated copper wire for powering the multiple cameras and light sources, while using a multimode (or single mode) optical fiber for high speed communication of multiple cameras through a USB hub. Such high speed optical communication means (using USB 3.0, USB 3.1, or higher bandwidth future USB communication standards), with transceivers at each end of the optical cable, serves as one example of a means for communicatively coupling the portable control and display unit to the camera(s) 201 and light source(s) 202, through a high speed USB hub, with one or more USB connections at the proximal housing 112.

Additionally, standard USB cables in conjunction with the flat cables are further communicatively coupled the portable control and display unit to the camera 201 and light sources 202, to communicate power and control signals between the portable control and display unit and the camera 201 and light sources 202. As such, the USB cable 106 further serves as an example of a means for communicatively coupling the portable control and display unit to the camera 201 and light sources 202 in a flexible and low profile format that can be routed seamlessly on the side of the port 701 at its proximal end without interference with other functionalities of the port 701 or device 904.

For any of the high digital speed communication methods used in (copper or optical) USB cable 106 between the display and control device and the camera 201 and light sources 202, appropriate USB connection can be made at the display and control unit, where the entire USB cable 106 can be also disposed of, along with the deployable camera 201 and light sources 202 that is housed at the distal section 101 of endoscope 100. Using standard USB communication protocols and connections to the display and control unit, allows the display and control unit to be or function as an off the shelf computing and processing unit such as a UMPC (Ultra Mobile Personal Computer), MID (Mobile Internet Device), a Tablet Computer, or mini PC or a PDA (Personal Digital Assistant), smart cellular phone (e.g. Nexus, iPhone, etc.), accommodating such USB communication port with or without additional USB power supply, such as power adapter or a battery. Use of such established video communication protocols such as UVC, for example in case of a high speed USB connection, makes the display and control unit a device readily available with multiple other connectivity solutions already available in a mobile form. Other wired connections could be Digital Video Interface (DVI), High Definition Multimedia Interface (HDMI), Ethernet connection, or external power adaptor connection, and wireless interfaces could be WiFi (wireless Ethernet), Bluetooth, Ultra Wide Band (UWB), IR, or high bandwidth cellular connection. Other portable or non portable computing and display units can be connected wirelessly, or with a wired connection, to the portable display and control unit.

Alternatively where a vision system with focusing or zoom capability is necessary, compact autofocus mechanism (lens actuator) could be also integrated into camera 201 housing, where certain or all imaging lenses 314 are to be moved axially with respect to the camera sensor, with drive and control signals from the control unit. Or otherwise a liquid lens (or liquid optical element) could be incorporated into the imaging lenses 314, where the optical power is changed by the control unit (or tremor and shaking of the image can be removed by the liquid optical element) in high speed. The control unit can be programmed to detect best focus or blurring of the image, due to vibrations in remote camera 201, with the imaging data it is provided from the camera 201 and can run it as if it is a local camera lens module within the control unit with autofocus, zooming, and vibration correction functionalities through the USB communication line.

A fully disposable, removable and pluggable camera 201 and light sources 202, implemented in the body of a single use, disposable distal section 101, can also be plugged onto, and electro-mechanically connected to the distal end of other single use or reusable medical device 1001a, medical device 1001b, or hollow access device 1101, which incorporates the flat actuation cables 206 and flat electrical cables 207 for electrical power, communication and means for deployment, enabling numerous multifunctional advantages. For instance, the pluggable endoscope plugged onto the distal end of a medical device 1001a or 1001b can also provide means for suction and delivery of liquid agents and medication by medical device 1001a or 1001b, and perform these function under the endoscope's concurrent visualization, in a fully sealed (air-tight) sterile cavity that can be disposed of after removal of distal section 101 containing the pluggable camera 201 and light sources 202 of the such medical device 1001a, 1001b or hollow access device 1101. Separating the distal section 101 from the medical device 1001a, medical device 1001b, or hollow access device 1101, disconnects the external power and control device it is used with on the USB cable 106, whereupon a new protected camera 201 and light sources 202 within a sterile distal section 101, can be plugged onto the distal tip of the medical device 1001a, medical device 1001b, or hollow access device 1101, and making new power and control device connection (and external sources of air, suction, lubrication or medication) for subsequent use, thereby eliminating the likelihood of contaminating body cavities in which the disposable medical devices are used.

Different or multiple camera 201 and light sources 202, with various functionalities, or in different spectrum of light, can be used in the multi jointed endoscope 100 or plugged on to a medical device 1001a, medical device 1001b, or hollow access device 1101, where a single deployable endoscope or multiple deployable endoscopes (such as 4 depicted in FIG. 12), on other medical tools or ports can be used concurrently inside the body. For instance, white light illumination or multi-spectral light sources 202 (containing multi chip Red Green Blue (RGB) LEDs that are individually controlled that can cover the visible spectrum) can be used for traditional imaging in the visible range, while light sources 202, with additional deep blue or UV illumination light sources 202 could be used to induce bio-fluorescence inside the body on the same deployable endoscope or a separate deployable endoscope.

The camera 201 could include a sensor for detecting spectral emission from the object at the same time as the visible imaging to gain further information regarding the object, such as the tissue type and identifying lesions. An IR illumination light source 202 can penetrate and image inside tissue or through scattering substances or fluids for an additional in-depth view. Different UV, visible and IR wavelength illumination light sources 202 with varying penetration depths can be used for depth dependent imaging inside the tissue. Various spectral components captured in 2D images can be subsequently processed and put together to reconstruct a 3D view of inside the body.

Concurrent image processing and correlation of multiple directional view points, from multiple imaging endoscopes such as the 4 deployed endoscopes depicted in FIG. 12, performed in real time by a common control and display unit that the multiple imaging endoscopes are connected and controlled as multiple USB cameras, allows 3D viewing of the object as well as better viewing through a liquid with scattering media (urine, or blood). For example the mixing and correlation of the 4 endoscope video output, observing the same location at the distal tip of a single port from slightly varying view angles, that are physically fixed relative to one another, allows the random noise in the images produced by a scattering media (liquid) in front of the cameras to be subtracted out in the combined common image that is processed in real time by the control and display unit.

The 4 endoscopes working concurrently in FIG. 12 could have similar illumination wavelengths or operate in various illumination wavelengths and bandwidths, providing different type of information detected by each of the endoscope cameras. Such combined and superimposed images of the 4 video output, processed and displayed by the same control and display unit running the 4 endoscopes as separate USB camera, can thus provide information much superior to viewing of an object with a traditional single white light endoscope that is routinely used.

LED light sources 202 can provide illumination in a wide range of the electromagnetic spectrum, from UV to visible and IR, where the individual LED chips, each with its own specific spectral wavelength range, can be independently controlled in time by software applications running in the control unit, and the corresponding spectral images can be independently processed by the control unit based on individual sensor captured frames, at the time where a specific wavelength LED chip is on. Each LED spectral component can be independently designed in the LED, or obtained with independent processing of each LED spectrum, via a secondary photo-luminescence process on blue or UV LEDs, or using edge or band pass spectral color filters such as multilayer dielectric optical filter coatings within the light sources 202. For imaging in the visible region, red, green, and blue LED chips in primary colors can be used in the light sources 202, with or without other non-primary colors such as amber or cyan where the multiple spectral LEDs together form a white illumination, adhering to a specific color gamut set by the control unit by adjusting individual LED drive electronics pulsing the individual LEDs (changing the LED light intensity by adjusting the pulse width of the drive modulation).

By using multiple color LED chips in the light sources 202 and synchronizing a black and white camera 201, equipped with global shutter, with the control unit to grab the synchronized color component images, the use of color camera chips or high resolution 3 CCD or 3 CMOS imaging devices are eliminated. In this case, a single CCD or CMOS image capture device is used to capture the three or more images in a time synchronized fashion, where each color component image takes advantage of the full image capture device resolution by incorporating all the pixels in each color image component. Simple black and white cameras are more sensitive and also cheaper to use, especially compared to 3 chip cameras, where in effect the resolution of a synchronized black and white imaging CCD or CMOS using synchronized color illumination provided by the LEDs is equivalent to a same pixel 3 chip camera.

Using a color synchronized camera 201 also allows the use of much higher resolution cameras 201 at the distal section 101. A variety of light sources 202 configurations are possible using multiple LED chips in the light sources 202, where the uniformity, angle and extent of the illumination are freely controlled by the positioning and design of the LED chips or optics in the light sources 202. Various fixed and deployable configurations are disclosed more fully in U.S. patent application Ser. No. 11/233,684, which is herein incorporated by reference.

A symmetrical dual channel, wavelength multiplexing geometry optics can be used as a stereo objective assembly in front of a single camera sensor, in conjunction with complimentary set of RGB illumination, in a Stereoscopic 3D implementation of endoscope using a single sensor as disclosed in U.S. Pat. No. 8,556,806, titled Wavelength Multiplexing Endoscope.

In current endoscopic imaging systems where a white light illuminator is used, the illumination spectrum is determined by the light source and the optical path the light is transmitted through before reaching the object inside the body. Subsequently, a 3-color camera (e.g., a single-chip RGB camera or 3-chip RGB camera) captures the reflected light from the object according to its RGB filter set and camera spectral sensitivity. An image display unit in turn displays the captured RGB image according to its own color filters.

IR chips, UV LED chips, or narrow spectral band VCSELs chips can be used in the light sources 202, based on their transmission and optical characteristics in the medium of insertion, such as wavelength dependent penetration depth inside the medium or based on the effect they have on the object of interest (such as inducing fluorescence). A diagnostic chemical agent can be sprayed (using spray catheter inserted through the same port or using spray nozzles at the distal tip of the disposable endoscope 100 through tubing from an external source, or internal reservoirs) and used to decipher cancerous cells from healthy cells in the Field of View (FOV) of the endoscope 100, when the scene under observation is illuminated by specific wavelength of light from the light sources 202, and where specific fluorescence light wavelength is detected by the sensor with commands and control from the control unit. Alternatively with dye injected into blood vessels, endoscope 100 with appropriate illumination wavelength can detect the florescence dye, locating veins.

With an endoscope 100 equipped with a full range of LED wavelengths in the light sources 202, or a specific range of illumination wavelength, it is possible to obtain full spectral images of the object by turning the various LEDs on and off at specified times with the control unit, and in a controlled spectral imaging range or color gamut of imaging depending on application, while a time synchronized imaging process in electronic processor in conjunction with the external control device, captures various spectral images based on the state of the light sources 202, at the time of image capture. The light sources 202 can be switched on and off on the same endoscope 100 or similar deployable endoscopes inserted into the body using other ports and tools at the same time.

In the case of surgical procedures where delicate and more precise diagnostic operation or surgery is performed using the endoscope, the camera 201 and light sources 202 can not only be made in minimal size, but can alternately or additionally house two or more miniature camera systems (directed towards the same FOV) with an extended dual USB device connection for stereoscopic view of the anatomy or surgical sight, with 3D viewing for extra precision and guidance with visual depth clues.

Incorporating disposable miniature solid state cameras 201 and light sources 202 in a deployable distal section 101 of a multi jointed endoscope 100, or on surgical disposable access device bodies that are rigid and flexible, without means for power of their own, not only eliminates device mounted displays, and large batteries used in portable devices, it also provides a highly desirable cost advantage over conventional lamp and fiber guide systems used in conventional endoscopes, as it replaces the expensive light sources, long fiber optic light guides to transfer illumination light from the light sources 202 to the scope, and the illumination light guides inside the scope as well. Low level power is needed for LED light sources, image sensors, and drive electronics. The electrical connection of the camera 201 and light sources 202, and their control is also much easier using USB type communication and power protocols, with well established mobile web camera applications in video conferencing.

Only electrical power and LED control signals need to be provided for the endoscope 100, eliminating the heavy and bulky batteries and fiber optics illumination cable connection to the scope, increasing the maneuverability, portability and, availability, and durability of the device in a fully sterile fashion anywhere, anytime. The low profile and flexibility of the flat actuation cables 206 and flat electrical cables 207, with a flexible multi-jointed body, can further enhance the maneuverability of other devices used in the same port or adjacent ports. Cameras 201 and light sources 202 are also more robust to shock and vibrations, or extreme environmental conditions, and practically unlimited shelf life and reliability than fiber optic illumination, traditional optics used in endoscopes that need to be cleaned and sterilized after each use, eliminating the need for an external camera systems.

In some embodiments of the invention, the cameras 201a and 201b and the light sources 202 are included within a single pluggable module to obtain stereoscopic viewing in a disposable stereoscopic access device or port 701. In these and other embodiments, the portable control and display unit can be used to house all the control electronics and software necessary to power the camera 201 and the light sources 202. The portable control and display unit may also include data transmission control (using standard network device protocol such as a USB host driving one or more web cameras with on board illumination), as well as any image processing and/or display functionalities. For instance, the portable control and display unit can include illumination and imaging control electronics that provide illumination and/or imaging control of multiple LED sources (individually, concurrently or in time) in the camera 201 and light sources 202. Alternately or additionally, the portable control and display unit can include image processing electronics that provide image processing of image data received from the camera 201, perform autofocus, or initiate drug and chemical agent delivery to the site from spray nozzles.

In some embodiments, the portable control and display unit can be a portable display unit used in a fixed position in a medical facility, or as a mobile application with an LCD, a touch screen, or other display unit capable of displaying 2D or 3D (stereoscopic) images. The portable control and display unit can alternately or additionally be worn by a user as a digital smart watch, eye glasses, or a cell phone, with a wired or wireless connection to the input devices (e.g., the camera 201 and the light sources 202), where the user can observe 2D or 3D stereo images and video on the wearable glasses, or by conveniently by looking at the display mounted on an arm of the user, hanging from a neck of the user, or otherwise mounted (clipped on) to the user or patient.

In some embodiments, the portable control and display unit can be electrically powered using a power cable, or use rechargeable or disposable batteries, with Optical USB cables connecting the endoscope vision system to a host computer, a separate medical system equipped with a USB port, or connected to a TV setup box (such as low cost and compact Android computer with HDMI, USB, Ethernet interfaces), displaying the video from the endoscope on TV displays. In similar possible embodiments, the electrical power supply of the portable control and display unit, whether from a power cable or battery, provides power for the portable control and display unit as well as the camera 201 and light sources 202 to which the portable control and display unit is attached via USB cable 106. Single camera 201 or multiple cameras 201a and 201b, and light sources 202 can be connected to the portable control and display unit (using USB hub like connections), which portable control and display unit can be configured to provide synchronized control of complete illumination and image capture for all connected cameras 201 and light sources 202 it is connected to. The portable control and display unit could also provide means for local and transferable means of image and video storage, with magnetic and/or electrical storage devices within its housing.

A user interface can be provided on the portable control and display unit and may include hard or soft electronic keys, a mouse or joystick, a touch screen, and/or voice activated command electronics. The user interface can be employed to adjust, control, display, process, transfer, store or retrieve the image and video data. The portable control and display unit can also electro-mechanically activate the flat actuator cables 206 to deploy or articulate the endoscope. The portable control and display unit can alternately or additionally comprise a multifunctional unit that is used as both a general portable medical display and one or more of: a cell phone, a mini computer with wireless or voice activation capabilities, mobile internet device (MID), a GPS unit, a personal digital assistant (PDA), a note-taking device, a dictation device, a video conferencing device, or the like.

The user interface devices described above, including hard or soft electronic keys, a mouse or joystick, a touch screen, and voice activated command electronics all serve as examples of input and/or output means that can be included in the portable control and display unit to communicatively control the endoscope functions and display the video form one or more endoscopes appropriately as a multi-window display solution. The portable control and display unit can alternately or additionally include computing means, such as a processor, microprocessor, controller, or the like. Alternately or additionally, the portable control and display unit can include cellular communication capabilities and/or wireless connectivity.

In some embodiments that include stereoscopic or 3D image capture, the portable control and display unit can display time-synchronized alternate left and right frames of the video from medical device vision modules, where a pair of time-synchronized liquid crystal shutters in front of the user's left and right eyes, allow each eye to see the corresponding alternating stereoscopic images. In such embodiments, the user can wear 3D-viewing time-synchronized shutter glasses with frame while viewing the 3D displayed data on the portable control and display unit, and while the 3D-viewing liquid crystal shutter glasses are time-synchronized with the portable control and display unit via a timing signal received via wireless interface (e.g., IR connection, Bluetooth) or hardwired connection, to the portable control and display unit.

Alternatively separate, non-overlapping bandpass RGB filtered glasses can view 3D images provided by two endoscopes, each equipped with matching separate, non-overlapping, bandpass RGB illumination in each of the endoscopes. Two sets of non-overlapping RGB light sources 202 can be used with RGB bandpass filter sets in front of two cameras 201a and 201b in FIG. 4, where matching non-overlapping RGB bandpass filter sets can be used by the user to view the 3D image on a single LCD monitor that in turn displays the two sets of alternating RGB left and right images with its own matching, and non-overlapping RGB back light illumination.

The portable control and display unit may comprise a flat panel LCD screen, touch screen, or other suitable screen such as organic LED display, 3D LCD that can display 3D stereoscopic images with or without special (polarized) glasses. A separate sterile disposable cover could be draping the portable control and display unit, preserving all user interface and electrical connection functionalities. Alternately or additionally, the portable control and display unit can have multiple positioning and attachment possibilities, depending on its size, the type of medical device it is used with, the type of medical procedure, the location the procedure is performed, and the type of user interface necessary. In fixed office or surgical environments, the portable control and display unit can be affixed to a wall, mounted on an IV post, clipped onto a patient cover or drape, or can be hung from a frame structure, with tilt, rotation, and locking capabilities and in a removable and portable form. Alternately or additionally, a fixed or portable control and display unit can be employed to control the camera 201 and the light sources 202 and/or to display image data captured by the camera 201, and wirelessly send the data to another display unit or TV.

Alternatively the control and display unit may be smart display eyeglasses that can be used for 2D and 3D viewing of the video, with voice activated controls. The active 2D/3D glasses used by the user can be connected using copper or fiber optic USB cable to the endoscope coupled to the USB cable 106 or wirelessly communicates the video signal with a control unit powering the endoscope light sources 202 and camera(s) 201.

In some embodiments, the portable control and display unit may be a wearable device that is attached to the arm or wrist of a user via a wearable attachment device or as a smart watch with computer on board. In more detail, a wide bracelet, wrist band or support structure, could be made of Velcro material, where a strip of mating Velcro could be fixed behind the portable control and display unit or its disposable cover. The Velcro arm band can be employed for adjustable attachment or wearing of the portable control and display unit on the arm or the wrist of the user.

In some embodiments, a disposable, rigid or flexible endoscope can use LEDs for illumination, solid state Laser Diodes (LD) or VSCELs can alternately or additionally be employed within the camera 201 and light sources 202 or independently at the distal end of pluggable single use endoscopes. For instance, Infrared (IR) Imaging employs IR solid state light sources to illuminate close tissue diagnostic and surgical procedures. IR detectors and special image sensors with modified optical filters or polarizers in front of their pixels can be employed as part of the camera and light source, for tissue and blood imaging along with IR light sources that have appreciable penetration depth in human tissue, blood or other bodily fluids, such as urine.

With the use of various wavelength LED chips (UV, visible spectra, or IR) in the light source, spectral imaging can be performed concurrently or at various time windows, and with spraying of the site with specific diagnostic agents using spray nozzles, under specific illumination wavelengths from the light source, tissue diagnosis relating the biofluorescence characteristics of the cells or imaging veins carrying fluorescent injected dye can also be performed on the area under observation. The surgical area under observation of the endoscope, can further be locally anesthetized or numbed with medication sprayed onto the site, from secondary devices 904, or medical device 1001 such as nozzles that are inserted into the port. Additional secondary devices 904 include surgical tools, such as biopsy needles or blood coagulating devices that can be inserted and used through the port 701 of FIG. 9.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An endoscope device comprising:
   a distal section that includes a housing with a first aperture, a second aperture, and an optically opaque barrier that separates the first aperture and the second aperture;
   a secondary section that includes a rotational hinge comprising a pivot pin and a guide pin disposed within the secondary section proximally relative to the rotational hinge, wherein the distal section is rotatably coupled to the secondary section through the rotational hinge, the rotational hinge defining an axis of rotation about which the distal section is configured to rotate relative to the secondary section, and wherein the guide pin is disposed within the secondary section at a location of the secondary section that is rigid;
   a light source positioned inside the first aperture and that is coupled to the housing, the light source configured to illuminate a body cavity;
   a digital camera sensor positioned inside the second aperture and that is coupled to the housing, the camera configured to capture images;
   a control unit in the secondary section; and
   a first thin flat cable electrically coupled with at least one of the digital camera sensor and the light source, and a second thin flat cable configured to actuate the distal section, wherein the first thin flat cable is routed between the pivot pin and the guide pin such that the first thin flat cable is in contact with the guide pin when the distal section is articulated relative to the secondary section, and the second thin flat cable is routed such that the guide pin is located between the first thin flat cable and the second thin flat cable.

2. The endoscope device of claim 1, wherein the first thin flat cable or the second thin flat cable or a third thin flat cable is physically fixed at the distal section, and adjustably connected to a tension spring at a proximal section, holding the distal section rotational hinge in a specific angle from the secondary section of the endoscope device, forming a triangular shape with respect to the distal section and the secondary section of the endoscope device.

3. The endoscope device of claim 1, further comprising an additional rotational hinge between the distal section and the proximal section of the endoscope device.

4. The endoscope device of claim 1, wherein the first thin flat cable and the second thin flat cable carry a MIPI serial output of the digital camera sensor to proximal housing electronics of the secondary section, where the MIPI serial output is converted to USB Video Class output format.

5. The endoscope device of claim 1, wherein the camera includes a digital camera with a Complementary Metal-Oxide Semiconductor (CMOS) sensor.

6. The endoscope device of claim 1, wherein the light source includes a light emitting diode or VCSEL of various wavelengths.

7. The endoscope device of claim 1, wherein the optically opaque barrier is configured to eliminate cross-talk between the light sources and the camera.

8. The endoscope device of claim 1, wherein the optically opaque barrier is configured to block stray light between the light sources and the camera.

9. The endoscope device of claim 1, wherein when the distal section is rotated, the first thin flat cable is routed distally with respect to the guide pin of the secondary section and the second thin flat cable is routed proximally with respect to the guide pin of the secondary section.

10. The endoscope device of claim 1, wherein the guide pin of the secondary section is configured to reduce tension in the first thin flat cable during bending of the rotational hinge.

11. The endoscope device of claim 1, wherein:
axes of the pivot pin and the guide pin are parallel to and spaced apart from each other;
the axes of the pivot pint and the guide pin lie in a common reference plane; and
the first thin flat cable is routed between the pivot pin and the guide pin such that the first thin flat cable extends through the common reference plane.

12. An endoscope device comprising:
a distal section that includes a housing with a first aperture, a second aperture, and an optically opaque barrier that separates the first aperture and the second aperture;
a secondary section that includes a rotational hinge comprising a pivot pin and a guide pin disposed within the secondary section proximally relative to the rotational hinge, wherein the distal section is rotatably coupled to the secondary section through the rotational hinge, the rotational hinge defining an axis of rotation about which the distal section is configured to rotate relative to the secondary section, and wherein the guide pin is disposed within the secondary section at a location of the secondary section that is rigid;
a light source positioned inside the first aperture and that is coupled to the housing, the light source configured to illuminate a body cavity;
a digital camera sensor positioned inside the second aperture and that is coupled to the housing, the camera configured to capture images;
a control unit in the secondary section; and
a first thin flat cable electrically coupled with at least one of the digital camera sensor and the light source and routed between the pivot pin and the guide pin;
a second thin flat cable configured to actuate the distal section in a first direction, the second thin flat cable routed to an opposite side of the guide pin from the first thin flat cable such that the guide pin is located between the first thin flat cable and the second thin flat cable; and
a third thin flat cable configured to actuate the distal section in a second direction opposite the first direction, the third thin flat cable routed to an opposite side of the pivot pin from the first thin flat cable such that the pivot pin is located between the first thin flat cable and the third thin flat cable.

13. The endoscope device of claim 12, wherein:
in response to the second thin flat cable being pulled proximally, the distal section is configured to rotate, relative to the second section, in the first direction; and
in response to the third thin flat cable being pulled proximally, the distal section is configured to rotate, relative to the secondary section, in the second direction.

14. The endoscope device of claim 12, wherein the first thin flat cable or the second thin flat cable or the third thin flat cable is physically fixed at the distal section, and adjustably connected to a tension spring at a proximal section, holding the distal section rotational hinge in a specific angle from the secondary section of the endoscope device, forming a triangular shape with respect to the distal section and the secondary section of the endoscope device.

15. The endoscope device of claim 12, further comprising an additional rotational hinge between the distal section and the proximal section of the endoscope device.

16. The endoscope device of claim 12, wherein the first thin flat cable and the second thin flat cable carry a MIPI serial output of the digital camera sensor to proximal housing electronics of the secondary section, where the MIPI serial output is converted to USB Video Class output format.

17. The endoscope device of claim 12, wherein the camera includes a digital camera with a Complementary Metal-Oxide Semiconductor (CMOS) sensor.

18. The endoscope device of claim 12, wherein the optically opaque barrier is configured to eliminate cross-talk between the light sources and the camera.

19. The endoscope device of claim 12, wherein the guide pin of the secondary section is configured to reduce tension in the first thin flat cable during bending of the rotational hinge.

20. An endoscope device comprising:
a distal section that includes a housing with a first aperture, a second aperture, and an optically opaque barrier that separates the first aperture and the second aperture;
a secondary section that includes a rotational hinge comprising a pivot pin and a guide pin disposed within the secondary section proximally relative to the rotational hinge, wherein the distal section is rotatably coupled to the secondary section through the rotational hinge, the rotational hinge defining a single axis of rotation about which the distal section is configured to rotate relative to the secondary section, and wherein the guide pin is disposed within the secondary section at a location of the secondary section that is rigid;
a light source positioned inside the first aperture and that is coupled to the housing, the light source configured to illuminate a body cavity;
a digital camera sensor positioned inside the second aperture and that is coupled to the housing, the camera configured to capture images;
a control unit in the secondary section; and
a first thin flat cable electrically coupled with at least one of the digital camera sensor and the light source and routed between the pivot pin and the guide pin; and
a second thin flat cable configured to actuate the distal section, the second thin flat cable routed to an opposite side of the guide pin from the first thin flat cable such that the guide pin is located between the first thin flat cable and the second thin flat cabled wherein in response to the second thin flat cable being pulled proximally, the distal section is rotatable from 0 degrees relative rotation to at least 90 degrees relative rotation about the single axis of rotation defined by the rotational hinge.

* * * * *